US011129553B2

(12) United States Patent
Kim et al.

(10) Patent No.: US 11,129,553 B2
(45) Date of Patent: *Sep. 28, 2021

(54) MOTION CAPTURE SYSTEM USING FBG SENSOR

(71) Applicants: KOREA INSTITUTE OF SCIENCE AND TECHNOLOGY, Seoul (KR); CENTER OF HUMAN-CENTERED INTERACTION FOR COEXISTENCE, Seoul (KR)

(72) Inventors: Jinseok Kim, Seoul (KR); Hyun Joon Shin, Seoul (KR); Bum-Jae You, Seoul (KR); Sungwook Yang, Seoul (KR); Minsu Jang, Seoul (KR); Jun Sik Kim, Seoul (KR)

(73) Assignees: Korea Institute of Science and Technology, Seoul (KR); Center of Human-Centered Interaction for Coexistence, Seoul (KR)

( * ) Notice: Subject to any disclaimer, the term of this patent is extended or adjusted under 35 U.S.C. 154(b) by 181 days.

This patent is subject to a terminal disclaimer.

(21) Appl. No.: 16/698,590

(22) Filed: Nov. 27, 2019

(65) Prior Publication Data

US 2020/0093404 A1 Mar. 26, 2020

Related U.S. Application Data

(62) Division of application No. 15/612,958, filed on Jun. 2, 2017, now Pat. No. 10,524,701.

(30) Foreign Application Priority Data

Jun. 8, 2016 (KR) ........................ 10-2016-0071010

(51) Int. Cl.
*A61B 5/11* (2006.01)
*A61B 5/00* (2006.01)
(Continued)

(52) U.S. Cl.
CPC .......... *A61B 5/1126* (2013.01); *A61B 5/0084* (2013.01); *A61B 5/1121* (2013.01);
(Continued)

(58) Field of Classification Search
CPC ..................... A61B 5/11–1135; A61B 5/4023
See application file for complete search history.

(56) References Cited

U.S. PATENT DOCUMENTS

| 9,423,311 B2 | 8/2016 | Moslehi |
| 2001/0021843 A1 | 9/2001 | Bosselmann et al. |

(Continued)

FOREIGN PATENT DOCUMENTS

| JP | 2001-518185 A | 10/2001 |
| JP | 2016-173365 A | 9/2016 |

(Continued)

*Primary Examiner* — Chu Chuan Liu
(74) *Attorney, Agent, or Firm* — Rabin & Berdo, P.C.

(57) ABSTRACT

A motion capture system includes a motion sensor having a flexible body and a fiber bragg gratings (FBG) sensor inserted into the body, a fixture configured to fix the motion sensor to a human body of a user, a light source configured to irradiate light to the motion sensor, and a measurer configured to analyze a reflected light output from the motion sensor, wherein the FBG sensor includes an optical fiber extending along a longitudinal direction of the body and a sensing unit formed in a partial region of the optical fiber and having a plurality of gratings, and wherein a change of a wavelength spectrum of the reflected light, caused by the change of an interval of the gratings due to a motion of the user, is detected to measure a motion state of the user.

18 Claims, 22 Drawing Sheets

(51) Int. Cl.
 *G01B 11/26* (2006.01)
 *G01L 1/24* (2006.01)
(52) U.S. Cl.
 CPC .......... *A61B 5/6804* (2013.01); *A61B 5/6847* (2013.01); *G01B 11/26* (2013.01); *G01L 1/246* (2013.01); *A61B 2562/0266* (2013.01)

(56) References Cited

U.S. PATENT DOCUMENTS

| | | |
|---|---|---|
| 2009/0137952 A1 | 5/2009 | Ramamurthy et al. |
| 2009/0217769 A1 | 9/2009 | Roberts |
| 2014/0268099 A1 | 9/2014 | Moslehi |
| 2015/0309563 A1 | 10/2015 | Connor |
| 2016/0273988 A1 | 9/2016 | Zhou |

FOREIGN PATENT DOCUMENTS

| | | |
|---|---|---|
| KR | 10-2006-0061564 A | 6/2006 |
| KR | 10-2009-0090910 A | 8/2009 |
| KR | 10-2013-0120206 A | 11/2013 |
| KR | 10-2014-0051554 A | 5/2014 |
| KR | 10-1498381 B1 | 3/2015 |
| KR | 10-2017-0023733 A | 3/2017 |

MOTION CAPTURE SYSTEM USING FBG SENSOR

CROSS-REFERENCE TO RELATED APPLICATION

This application claims priority to Korean Patent Application No. 10-2016-0071010, filed on Jun. 8, 2016, and all the benefits accruing therefrom under 35 U.S.C. § 119, the contents of which in its entirety are herein incorporated by reference.

This application is a divisional of U.S. application Ser. No. 15/612,958, filed on Jun. 2, 2017, which is incorporated by reference in its entirety.

BACKGROUND

1. Field

The present disclosure relates to a motion capture system, and more particularly, to a motion capture system for measuring a motion state of a user by analyzing a wavelength spectrum of light using a fiber bragg gratings (FBG) sensor.

DESCRIPTION ABOUT NATIONAL RESEARCH AND DEVELOPMENT SUPPORT

This study was supported by the Global frontier Project of National Research Foundation of Korea (Project Name. Development of wearable 3D motion capturing human interface technology, Project No. 2015076511) under the superintendence of Ministry of Science, ICT and Future Planning, Republic of Korea.

2. Description of the Related Art

Motion capture is a work for recording a motion of a human body in a digital form by attaching a sensor to the human body or using a camera.

The motion of a human body recorded in a digital form may be used as a control value for controlling a motion of a virtual averter or a humanoid slave robot in a human-centered interaction system.

Representative motion capture techniques include camera-based techniques such as a technique of photographing a target using a plurality of cameras and then matching a plurality of camera images, or a technique of attaching an optical marker to a human body and photographing the optical marker with a camera.

However, these techniques using cameras have a limitation in space for installing the cameras, and a shaded area which cannot be partially photographed by the cameras may be generated. Thus, accurate motion capturing is difficult.

In addition, it is difficult to accurately capture motions of body organs, such as hands, which make elaborate movements in combination of several joints.

Therefore, in existing motion capture techniques, it is substantially impossible to control a very precise motion, for example in a case where two averters controlled by two users shakes hands with each other in a single virtual space, which needs angles and positions of the hands of the averters to be exactly matched.

In order to compensate for this, a motion capture technique for attaching an inertial measurement unit (IMU) sensor to knuckles connected through a joint and calculating an angle of the like of the joint through a measurement value of the IMU sensor has been designed.

However, even with the motion capture method using the IMU sensor, there is still a limitation in capturing a small and elaborate motion of a joint, like the hand, due to the number, type, size and measurement position of the IMU sensors.

In addition, due to the use of an electronic IMU sensor, a so-called "drift phenomenon" occurs due to an error caused when the sensor is used for a long period of time, and thus long-time use is unavailable.

RELATED LITERATURES

Patent Literature

Korean Unexamined Patent Publication No. 10-2006-0061564

SUMMARY

The present disclosure is directed to providing a motion capture system which may capture a motion of a whole human body without a limitation in space and a blind spot in measurement, avoid error accumulation caused by long-time use, and be able to capture a complicated and elaborate motion of a human body.

In one aspect of the present disclosure, there is provided a motion capture system, comprising: a motion capture system, comprising: a motion sensor having a flexible body and a plurality of fiber bragg gratings (FBG) sensors inserted into the flexible body; a fixture configured to fix the motion sensor to a human body of a user; a light source configured to irradiate light to the motion sensor; and a measurer configured to analyze a reflected light output from the motion sensor, wherein each of the FBG sensors includes an optical fiber and a sensing unit formed in a partial region of the optical fiber and having a plurality of gratings, wherein the motion sensor includes one or more of an angle detection sensor and an angle/direction detection sensor, the angle detection sensor being configured to measure an angle for a 1-DOF (degree of freedom) joint which is bendable only in one direction, the angle/direction detection sensor being configured to measure motions of a multi-DOF joint which is bendable in a plurality of directions, wherein the angle/direction detection sensor is further configured to measure a presence of rotation and a rotation amount by calculating a position change of a tip of the sensing unit, and wherein a change of a wavelength spectrum of the reflected light, caused by a change of an interval of the gratings due to a motion of the user, is detected to measure a motion state of the user.

According to an embodiment, the sensing unit of the motion sensor may be further configured to be disposed on a joint of the user, and the motion sensor may include the sensing unit to calculate a bending angle of the joint by means of the change of the wavelength spectrum.

According to an embodiment, the angle/direction detection sensor may include the sensing unit to calculate a bending angle, a bending direction and a rotating direction of a joint of the human body by means of the change of the wavelength spectrum.

According to an embodiment, the sensing unit of the angle detection sensor may be configured to be disposed at the 1-DOF (degree of freedom) joint which is bendable only in one direction.

According to an embodiment, the sensing unit may include a plurality of grating nodes each having a plurality of gratings, the plurality of gratings are arranged at a same interval in each of the plurality of grating nodes, and intervals between gratings of the grating nodes are different for each grating node.

According to an embodiment, the angle detection sensor may include a plurality of FBG sensors, a longitudinal central axis of the plurality of FBG sensors may be spaced apart from a longitudinal central axis of the flexible body, and the grating nodes of the FBG sensors along the longitudinal direction of the angle detection sensor may be located not to overlap each other.

According to an embodiment, the body may have a quadrilateral cross section, when being observed in a longitudinal direction.

According to an embodiment, the sensing unit of the angle/direction detection sensor may be configured to be disposed at the 1-DOF joint which is bendable in only one direction, at a multi-DOF joint which is bendable in a plurality of directions, or at a part of the human body which is rotatable based on a single joint.

According to an embodiment, the angle/direction detection sensor may include a plurality of FBG sensors, and a longitudinal central axis of the plurality of FBG sensor may be spaced apart from a longitudinal central axis of the flexible body.

According to an embodiment, the angle/direction detection sensor may include three FBG sensors provided at an interval of 120 degrees based on the longitudinal central axis of the flexible body.

According to an embodiment, the sensing unit may include a plurality of grating nodes each having a plurality of gratings, the plurality of gratings are arranged at a same interval in each of the plurality of grating nodes, and intervals between gratings of the grating nodes are different for each grating node.

According to an embodiment, the angle/direction detection sensor may is configured to be extend to surround the human body between joints, and the sensing unit of the angle/direction detection sensor may be configured to be disposed at the human body between the joints.

According to an embodiment, the motion sensor may include a plurality of sensing units, respective sensing units having different intervals between gratings, and the plurality of sensing units may be configured to be disposed corresponding to different portions of the human body.

According to an embodiment, the fixture may include a band configured to surround knuckles connected through the joint, and the flexible body of the motion sensor extending in both directions based on the sensing unit may be tightly fixed to two bands formed at two knuckles connected through the joint.

According to an embodiment, the motion sensor may be attached to the fixture, and the fixture may be cloth which is wearable by the user.

According to an embodiment, the motion capture system may be configured to be worn on the human body by modularization on required body portions.

According to an embodiment, each of motion sensors of modules for the modularization may be connected to control boxes, respectively.

According to an embodiment, a control box sized to carry on a waist of the user, including a light source, connector and a measurer, the connector connecting the motion sensor with the light source.

According to an embodiment, the flexible body of the angle detection sensor may has a quadrilateral cross section or the angle/direction detection sensor may be radially arranged.

DETAILED DESCRIPTION

Figure 1:
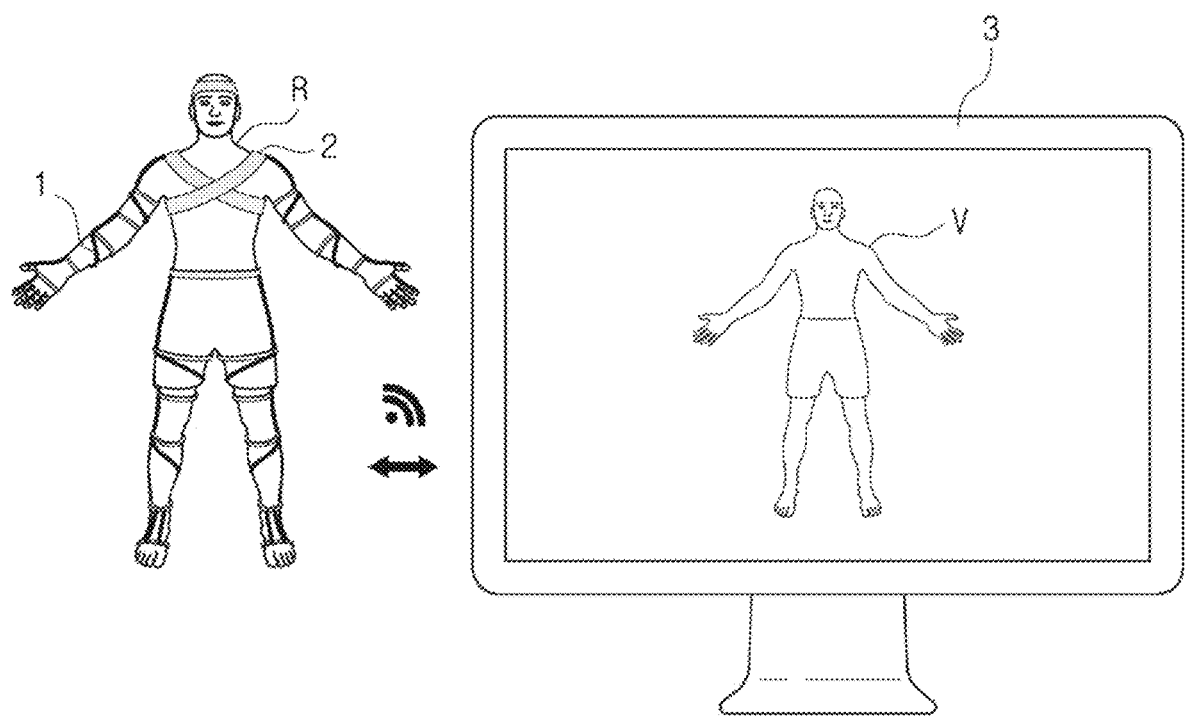
FIG. 1 shows a motion capture system according to an embodiment of the present disclosure.

Hereinafter, an embodiment of the present disclosure will be described with reference to the drawings. Even though the present disclosure is described based on the embodiment depicted in the drawings, this is just an example, and the essential configuration and operations of the present disclosure are not limited thereto.

FIG. 1 shows a motion capture system according to an embodiment of the present disclosure.

According to this embodiment, the motion capture system includes a plurality of motion sensors 1 extending to each joint of a user R and having an elongated wire shape, and a fixture 2 for fixing the motion sensor 1 to a body of the user R.

A motion of the joint of the user R is measured using the motion sensor 1, and the collected motion data of the joint may be used for controlling a motion of an averter V placed at a virtual reality in a display device 3. Furthermore, in addition to a graphic formed in the virtual space, an object replicating the motion of the user, such as a slave robot, may also be used as the averter.

The motion sensor 1 of this embodiment may include two kinds of sensors, namely an angle detection sensor 100 capable of measuring a bending angle of a joint of the user and an angle/direction detection sensor 200 capable of calculating a bending angle, a bending direction and a rotating direction of a body of the user.

According to this embodiment, both the angle detection sensor 100 and the angle/direction detection sensor 200 include a flexible body and a fiber bragg gratings (FBG) sensor, inserted into the body.

Hereinafter, the angle detection sensor 100 and the angle/direction detection sensor 200 will be explained first.

Figure 2A:
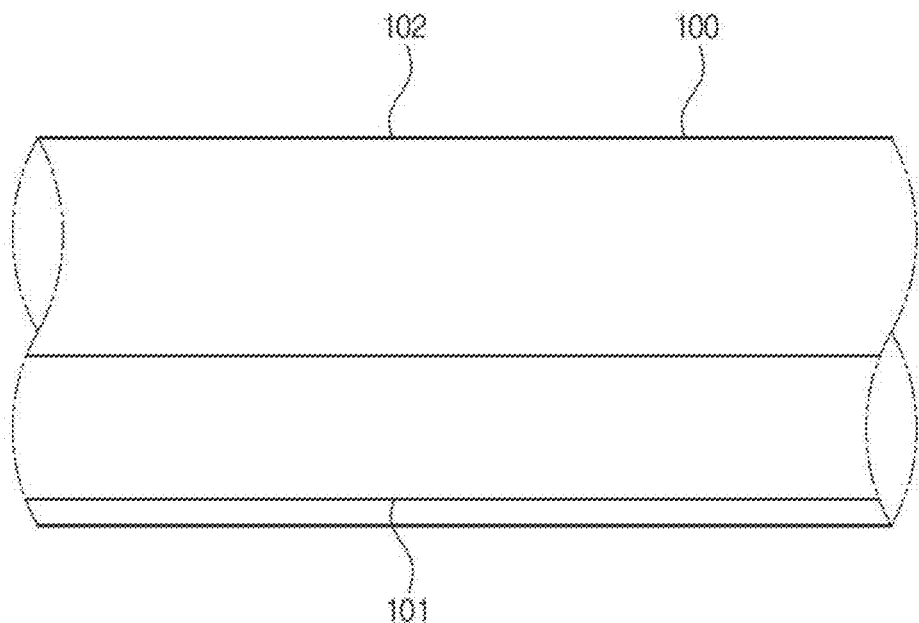
FIGS. 2A and 2B shows an angle detection sensor according to an embodiment of the present disclosure.
Figure 2B:
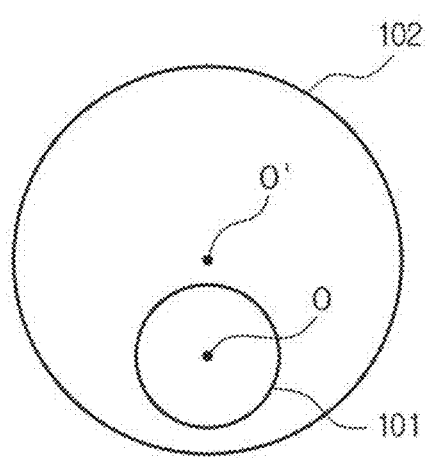

FIGS. 2A and 2B shows the angle detection sensor 100 according to an embodiment of the present disclosure.

The angle detection sensor 100 of this embodiment includes an elongated flexible body 102 made of epoxy resin and a single-stranded FBG sensor 101 disposed in the body 102 along a longitudinal direction of the body 102.

As explained later, in the motion sensor, the FBG sensor is bent according to a motion of a joint to change an interval between gratings. A change of a wavelength spectrum of a reflected light generated from this change is detected to measure the motion of the joint.

If the center of the FBG sensor is identical to a bending center O' of the angle detection sensor 100, since an average of changes of the grating intervals based on the center of the FBG sensor becomes 0 (based on the center of the FBG sensor, an interval between adjacent two gratings increases at one portion, but an interval between adjacent two gratings decreases at an opposite portion, and thus the average change of the intervals substantially becomes 0), an accurate bending state is not calculated.

Therefore, as shown in FIG. 2B, the center (the core center) of the FBG sensor 101 of this embodiment is spaced apart from the bending center O' of the entire angle detection sensor 100.

Figure 3:
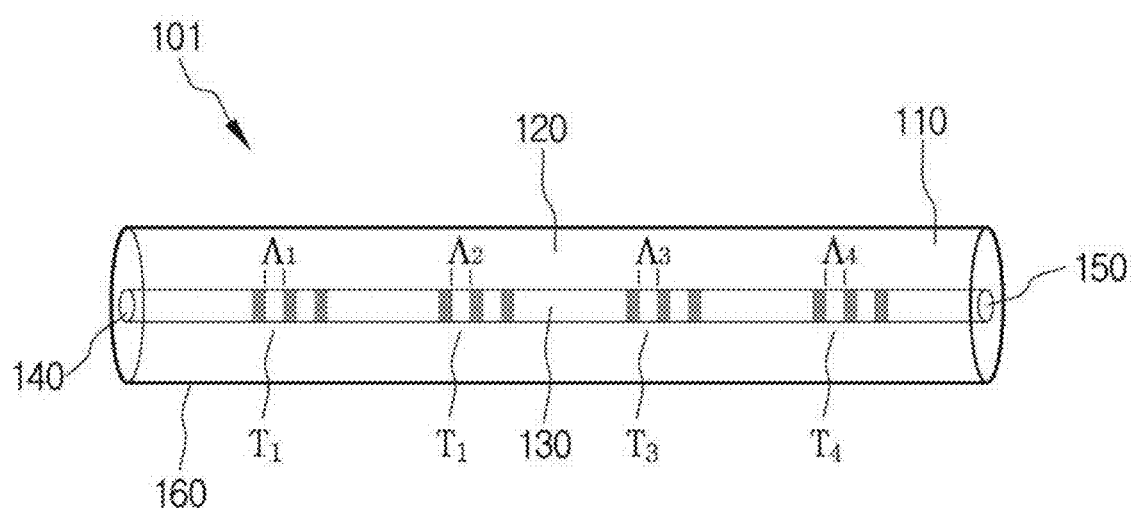
FIG. 3 shows a configuration of a fiber bragg gratings (FBG) sensor used in a motion sensor.

FIG. 3 shows a configuration of the FBG sensor 101 used in a motion sensor.

The FBG sensor 101 is made of an optical fiber 110, and a sensing unit 160 having a plurality of gratings is formed in a partial region of the optical fiber 110.

In FIG. 3, only the sensing unit 160 including gratings $T_1$ to $T_4$ in a partial region of the optical fiber is depicted. In the actual FBG sensor, the optical fiber is elongated based on the sensing unit 160.

The optical fiber 110 includes a cladding 120 made of glass material and configured to freely bend, and a core 130 formed at a center of the cladding 120 along a longitudinal direction of the cladding 120. A refractive index of the cladding 120 is different from a refractive index of the core 130. A light inlet 140 and a light outlet 150 are formed at both ends of the optical fiber 110 so that light is input from a light source (not shown) and also light passing through the core 130 is output.

At the core 130 of the sensing unit 160, a plurality of grating nodes $T_1$ to $T_4$ (formed by grouping an n (n≥2, natural number) number of gratings) are formed.

The grating is prepared by changing properties of a part of the core 130 by using UV rays when the optical fiber 110 is being manufactured, and the grating has a refractive index different from those of the cladding 120 and the core 130.

The gratings forming each grating node $T_1$ to $T_4$ are arranged at the same interval. Intervals $\Lambda_1$ to $\Lambda_4$ between gratings of each grating node ($T_1$ to $T_4$) are gradually increasing (namely, $\Lambda_1 < \Lambda_2 < \Lambda_3 < \Lambda_4$). Intervals between grating nodes are much greater than the intervals $\Lambda_1, \Lambda_2, \Lambda_3, \Lambda_4$ of the gratings forming each grating node.

According to the above configuration, the light incident on the light inlet 140 of the optical fiber 110 is interfered by the grating nodes. The reflected light output back to the light inlet 140 shows a wavelength spectrum having a peak corresponding to each grating node.

Figure 4:
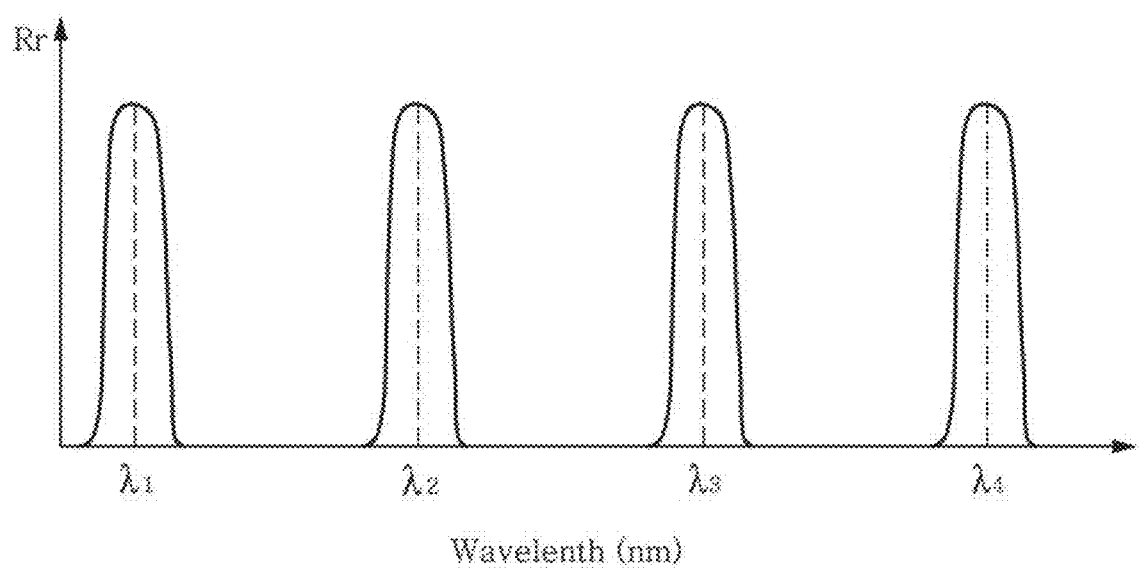
FIG. 4 is a graph showing a wavelength spectrum of a reflected light output to a light inlet of the FBG sensor of FIG. 3.

FIG. 4 is a graph showing a wavelength spectrum of a reflected light output to the light inlet 140 of the FBG sensor 101.

The grating interval $\Lambda$ of the grating nodes and the wavelength $\lambda_B$ of the reflected light have a relationship as in Equation 1 below.

$$\lambda_B = 2 \cdot n_{eff} \cdot \Lambda \qquad \text{[Equation 1]}$$

Here, $n_{eff}$ is an indicator showing an effective refractive index of the core.

The wavelengths $\lambda_1, \lambda_2, \lambda_3, \lambda_4$ appearing in the wavelength spectrum of FIG. 4 correspond to the values obtained by substituting the intervals $\Lambda_1, \Lambda_2, \Lambda_3, \Lambda_4$ of the gratings of each grating node into Equation 1. In other words, the wavelengths $\lambda_1, \lambda_2, \lambda_3, \lambda_4$ represent wavelengths of the reflected light which is reflected by a single grating node and then output, respectively.

If the optical fiber 110 is bent at the position where the first grating node T1 is located, the interval $\Lambda_1$ of the gratings of the first grating node $T_1$ will be changed. Accordingly, it may be observed that the curve with respect to the wavelength $\lambda_1$ shifts to the right or the left, among the wavelength curves of FIG. 4, by the relation of Equation 1 above. If it is observed that the curve with respect to the wavelength Ai shifts to the right or the left, it may be understood that the optical fiber is bent at the position of the first lattice node $T_1$.

As described above, the wavelength $\lambda_B$ of the reflected light output from the FBG sensor 101 is proportional to the interval $\Lambda$ of the gratings.

Since the change of the interval $\Lambda$ of the gratings reflects the strain ε of the sensing unit 160 of the FBG sensor 101, a curvature (bending degree) of the sensing unit 160 of the optical fiber 110 may also be known using the same.

Figure 5:
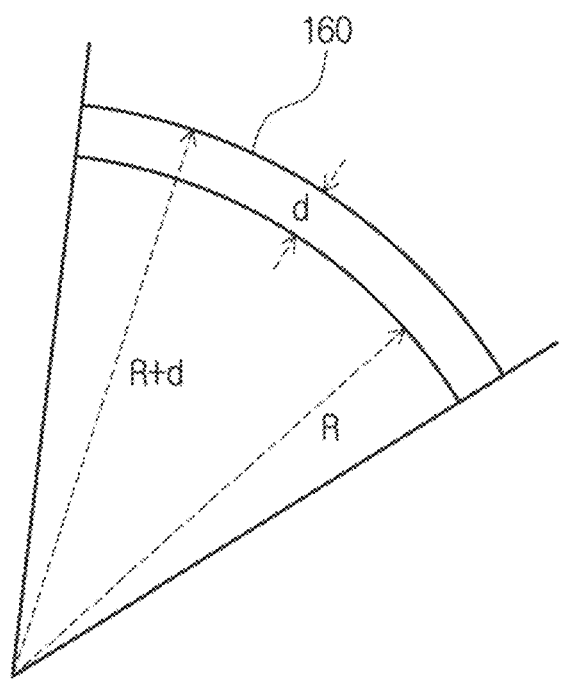
FIG. 5 shows that an angle detection sensor is partially bent.

FIG. 5 shows that the angle detection sensor 160 is partially bent.

As shown in FIG. 5, assuming that the diameter of the optical fiber 110 is d and the curvature of the sensing unit 160 is k (k=1/R), the strain ε of the sensing unit 160 may be expressed as Equation 2 below.

$$\varepsilon = \frac{\Delta L}{L} = \frac{(R+d)\theta - R\theta}{R\theta} = \frac{d}{R} \qquad \text{[Equation 2]}$$

By using the above principle, a bending angle of the joint may be calculated from the change of the spectrum.

Figure 6:
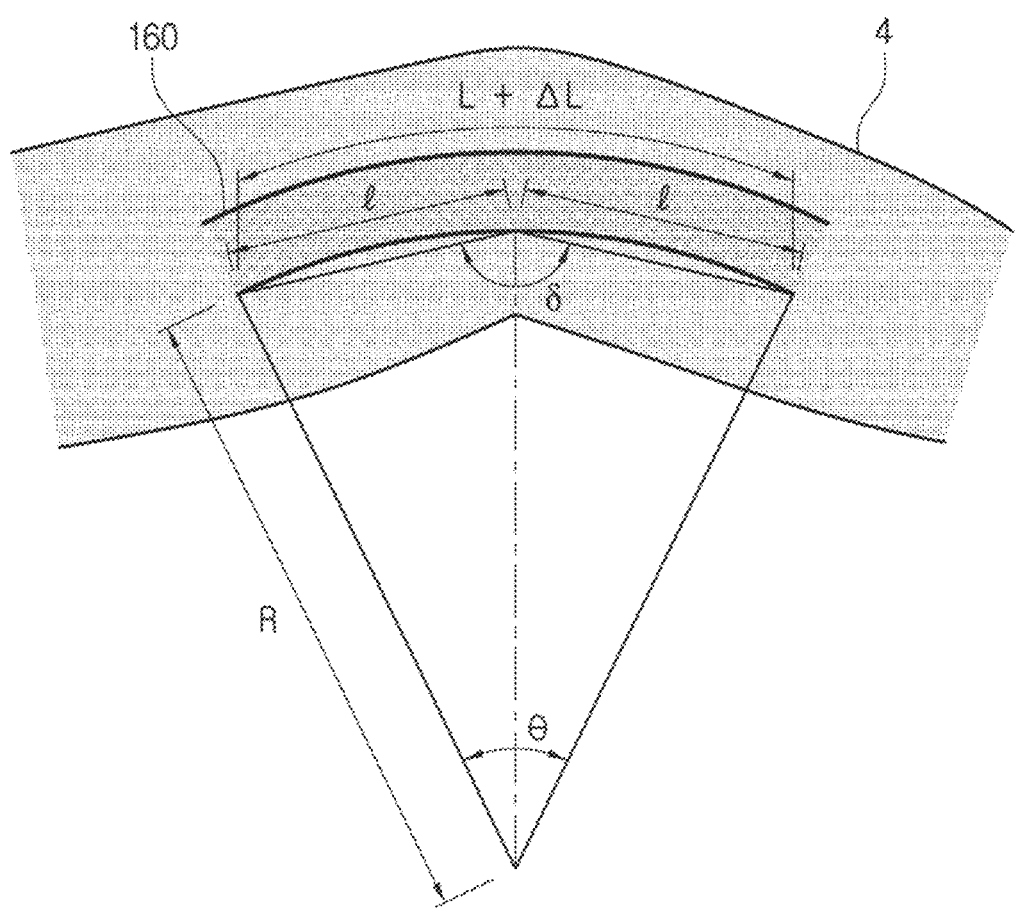
FIG. 6 shows that the angle detection sensor of FIG. 2A is applied to a joint of a finger.

FIG. 6 shows that the angle detection sensor 100 is applied to a joint of the finger 4.

The angle detection sensor 100 extends along a side of a finger 4 so that the sensing unit 160 is disposed at a location of a joint.

When the finger 4 is stretched, the sensing unit 160 has a straight form, and when the joint of the finger is bent, the sensing unit 160 is bent correspondingly. The bending degree of the sensing unit 160 is proportional to the joint bending angle of the finger.

When the joint of the finger is bent, the sensing unit 160 is bent, and the interval between the gratings belonging to the sensing unit 160 is changed, which also changes the wavelength spectrum of the reflected light.

According to this embodiment, a central portion of the sensing unit 160 in the longitudinal direction is aligned at the joint position of the finger.

Thus, the joint angle δ of the finger may be defined as an angle between two line segments of length l connecting one end and the center of the bent sensing unit 160.

A radius R may be found from the relationship between an original length L of the sensing unit 160 and a length ΔL which increases according to the bend as in Equation 2, and θ may be calculated since θ meets the following equation: θ=k (L+ΔL) (k=1/R).

Further, a bending angle δ of the finger joint may be obtained as in Equation 4 below.

$$\delta = 2\arcsin\left(\frac{\cos(\theta/2)}{\theta/2}\right)$$ [Equation 4]

In other words, the curvature of the sensing unit 160 may be calculated through the analysis of the wavelength spectrum of the reflected light, and the bending angle of the finger joint may be calculated therefrom.

However, Equation 4 is just an example, and the relationship between the curvature and the bend angle may also be changed by the position of the angle detection sensor 100 with respect to the finger, the number of grating nodes belonging to the sensing unit 160, and the interval of grating nodes.

In addition, a correcting work for compensating a difference between the bending angle of the joint calculated by the angle detection sensor 100 installed on the finger and an actually measured bending angle may be required.

Figure 7A:
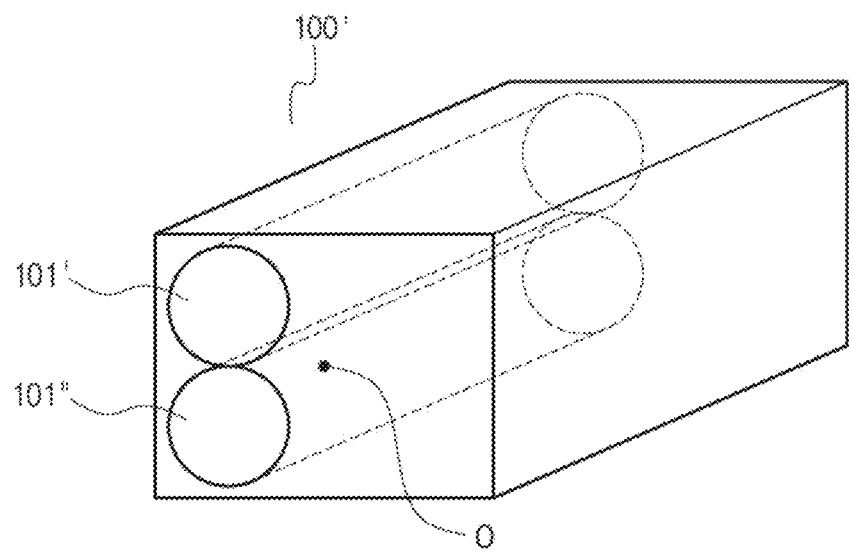
FIGS. 7A and 7B shows an angle detection sensor according to another embodiment.
Figure 7B:
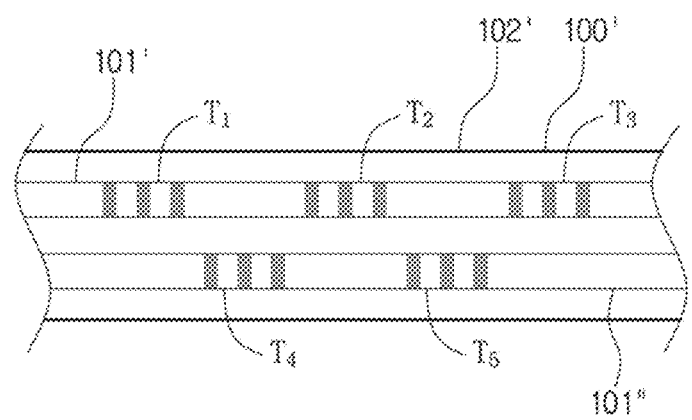

FIGS. 7A and 7B shows an angle detection sensor 100' according to another embodiment.

In the former embodiment, the angle detection sensor is constructed using a single FBG sensor 100. As shown in FIG. 3, a predetermined interval is present between the grating nodes of the FBG sensor 100. This interval is a so-called dead zone.

If the joint of the finger 4 is located at the dead zone, the interval between the gratings may not increase corresponding to the bending motion of the joint of the finger. The accuracy of measuring the bending angle of the joint may be reduced as much.

Therefore, according to this embodiment, the angle detection sensor 100' includes two FBG sensors 101', 101" whose centers in the longitudinal direction center are spaced apart with respect to the bending center O of the body 102'.

As shown in FIG. 7B, the grating nodes $T_1$, $T_2$, $T_3$ of the first FBG sensor 101' and the grating nodes $T_4$, $T_5$ of the second FBG sensor 101" in the sensing unit of the angle detection sensor 100' are alternately arranged so that their positions along the longitudinal direction of the angle detection sensor 100' do not overlap with each other.

Accordingly, it is possible to minimize that the joint bending position of the finger 4 is located in the dead zone.

The grating nodes $T_1$, $T_2$, $T_3$ of the first FBG sensor 101' and the grating nodes $T_4$, $T_5$ of the second FBG sensor 101' have different intervals.

Meanwhile, as shown in FIG. 7A in a best way, the body 102' has a quadrilateral cross-section when being observed in longitudinal direction. Accordingly, the angle detection sensor 100' may be more closely fixed to a side of the joint of the human body.

When the body of the angle detection sensor is made in a circular shape, the body may be fixed to a fixing band or chute to give the directionality. However, when the body is made to have a quadrilateral cross section, the sensor has a bending direction in itself, and thus the bending direction of the sensor may not be taken into consideration.

The angle detection sensor 100 of this embodiment is formed to extend along the side of the finger 4 so that the sensing unit 160 extends over the joint position, without being limited thereto.

If the sensing unit 160 may be bent corresponding to the motion of the joint, the angle detection sensor 100 may also be arranged to pass through the joint at any position of a human body. The relationship between the curvature and the bending angle detected from the sensing unit 160 may be determined according to the position of the angle detection sensor 100 based on the actually measured information of the bending angle of the joint according to the detected curvature.

Figure 8A:
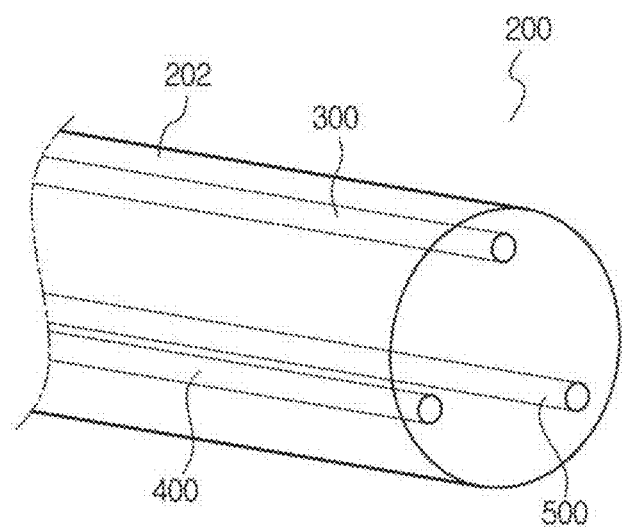
FIGS. 8A and 8B shows an angle/direction detection sensor according to an embodiment of the present disclosure.
Figure 8B:
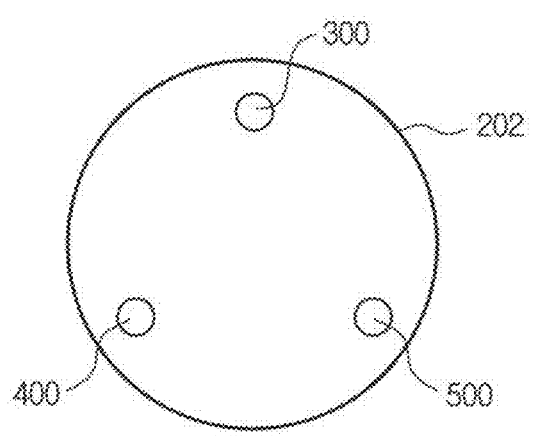

FIGS. 8A and 8B shows the angle/direction detection sensor 200 according to an embodiment of the present disclosure.

The angle/direction detection sensor 200 of this embodiment has a plurality of FBG sensors as described above, and may detect the curvature and the bending direction of the body of the sensor 200 by using the change of the wavelength spectrum of the reflected light for each FBG sensor.

As shown in FIGS. 8A and 8B, in the body 202 of the angle/direction detection sensor 200 of this embodiment, three FBG sensors 300, 400, 500 are formed.

There FBG sensors 300, 400, 500 are radially arranged about the center O of the body 202 in the longitudinal direction and are formed at the same interval with an angle of 120°. Thus, the centers of the FBG sensors 300, 400, 500 (the core centers) are spaced apart from the bend center of the entire angle/direction detection sensor 200.

Figure 9:
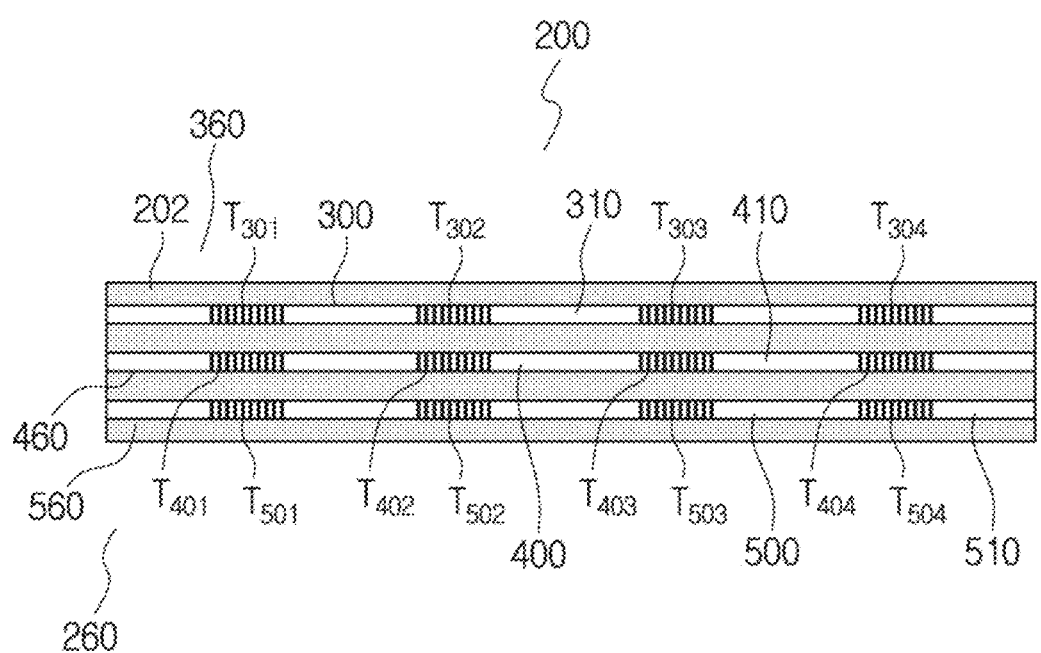
FIG. 9 is a side view showing the angle/direction detection sensor of FIG. 8.

FIG. 9 is a side view showing the angle/direction detection sensor 200. For convenience of explanation, three FBG sensors 300, 400, 500 are shown without distinguishing between optical fibers and cores. Also, FIG. 9 shows only the sensing unit 260, which is a partial region of the optical fiber including the grating. The actual angle/direction detection sensor 200 is shaped so that the optical fiber is elongated about the sensing unit 260.

A plurality of grating nodes $T_{301}$, $T_{302}$, $T_{303}$, $T_{304}$ are formed in the sensing unit 360 of the optical fiber 310 of the first FBG sensor 300. The gratings forming each grating node $T_{301}$, $T_{302}$, $T_{303}$, $T_{304}$ are arranged at the same interval. The intervals between the gratings forming each grating node $T_{301}$, $T_{302}$, $T_{303}$, $T_{304}$ are different from each other and have an increasing relationship in this embodiment.

A plurality of grating nodes $T_{401}$, $T_{402}$, $T_{403}$, $T_{404}$ are formed in the sensing unit 460 of the optical fiber 410 of the second FBG sensor 400. The gratings forming each grating node $T_{401}$, $T_{402}$, $T_{403}$, $T_{404}$ are arranged at the same interval. The intervals between the gratings forming each grating node $T_{401}$, $T_{402}$, $T_{403}$, $T_{404}$ are different from each other and have an increasing relationship in this embodiment.

A plurality of grating nodes $T_{501}$, $T_{502}$, $T_{503}$, $T_{504}$ are formed in the sensing unit 560 of the optical fiber 510 of the third FBG sensor 500. The gratings forming each grating node $T_{501}$, $T_{502}$, $T_{503}$, $T_{504}$ are arranged at the same interval. The intervals between the gratings of each grating node $T_{501}$, $T_{502}$, $T_{503}$, $T_{504}$ are different from each other and have an increasing relationship in this embodiment.

If the change of wavelength of the reflected light of each corresponding sensor is detected from the sensing units 360, 460, 560 of three FBG sensors 300, 400, 500, information on the curvature and the bending direction of the sensing unit 260 may be obtained.

Figure 10:
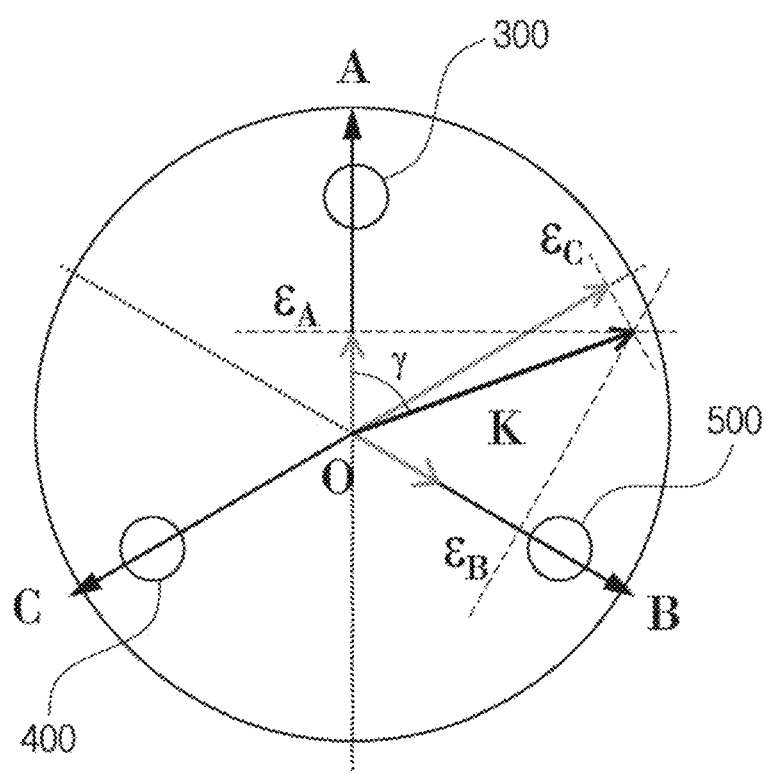
FIG. 10 is a diagram for illustrating a principle of detecting a bending direction in the angle/direction detection sensor of FIG. 8.

FIG. 10 is a diagram for illustrating a principle of detecting a bending direction in the angle/direction detection sensor 200.

In FIG. 10, the first FBG sensor 300 is indicated by a subscript A, the second FBG sensor 400 by a subscript B, and the third FBG sensor 500 by a subscript C, for convenience in formulating.

When a partial portion of the sensing unit 260 of the angle/direction detection sensor 200 is bent, the wavelength of the reflected light corresponding to the grating node located near the bend portion of each FBG sensor 300, 400, 500 is changed.

At this time, the strains E of the FBG sensors 300, 400, 500 are different from each other depending on the bending direction. For example, in FIG. 10, when the body is bent in a downward direction, the grating node of the corresponding portion of the first FBG sensor 300 will have an increased interval, and the grating nodes of the corresponding portions of the other FBG sensors 400, 500 will have a reduced interval.

If the strains E of the FBG sensors 300, 400, 500 are compared, the curvature k of the sensing unit 260 in the bent portion may be calculated as shown in Equation 5 below, and the bending direction y may be calculated as shown in Equation 6 below.

$$\kappa = \frac{1}{d}\sqrt{\left(\frac{2\varepsilon_A - \varepsilon_B - \varepsilon_C}{3}\right)^2 + \left(\frac{\varepsilon_B - \varepsilon_C}{\sqrt{3}}\right)^2} \quad \text{[Equation 5]}$$

$$\gamma = \arctan\left(\frac{\sqrt{3}\,(\varepsilon_B - \varepsilon_C)}{2\varepsilon_A - \varepsilon_B - \varepsilon_C}\right) \quad \text{[Equation 6]}$$

Where $\varepsilon_A$ is a strain of the first FBG sensor 300 in the bent region, $\varepsilon_B$ is a strain of the second FBG sensor 400 in the bent region, and $\varepsilon_C$ is a strain of the third FBG sensor 500 in the bent region.

If the wavelength spectrums of the reflected lights output from the FBG sensors 300, 400, 500 of the angle/direction detection sensor 200 are analyzed, it may be found which portion of the sensing unit 260 is bent and strained, and its curvature and bending direction may be found using Equations 5 and 6.

It has been described above to calculate the bending angle of the joint that bends the sensing unit through the curvature of the sensing unit. In addition, the bending direction of the sensing unit shows a bending direction of the joint that deflects the sensing unit.

Thus, for example, if the angle/direction detection sensor 200 is placed at a joint that may be bent in various directions, like a wrist, and the sensing unit 260 is fixed to be bent corresponding to the motion of the wrist joint, the bending angle and the bending direction of the wrist joint may be known from the curvature and the bending direction of the sensing unit 260.

However, even though the angle/direction detection sensor 200 is applied to a joint so that the sensing unit 260 is disposed at a position corresponding to the joint, the present disclosure is not limited thereto.

For example, an upper arm connected to the shoulder is rotated (warped) based on an axial direction of the shoulder joint.

For example, if the angle/direction detection sensor 200 is arranged diagonally along the upper arm and the sensing unit 260 is disposed to be in contact with the skin of the upper arm, the length of each grating node of the sensing unit 260 is changed according to the rotation of the upper arm in response to the motion of a portion of the human body where each grating node is located.

If the wavelength spectrum signal detected from each grating node is analyzed, the bending direction of a portion where each grating node is located is calculated. If the corresponding bending directions are combined, the change of shape of the angle/direction detection sensor 200 based on a reference point (the shoulder joint) may be measured, and from this, the position change of a tip of the sensing unit may be calculated, which allows to measure the presence of rotation and the rotation amount.

Meanwhile, even though the angle/direction detection sensor 200 of this embodiment has been described as having three FBG sensors, the present disclosure is not limited thereto.

For example, referring to FIG. 10, by disposing the first FBG sensor 300 and the second FBG sensor 400 so that the second FBG sensor 400 forms an angle of 90 degrees with respect to the center O of the first FBG sensor 300, the bending direction of the sensing unit may be known using two FBG sensors.

In FIG. 10, when the sensing unit is deflected in a direction A, the grating interval of grating nodes located in the bent region of the first FBG sensor 300 decreases. Thus, it is possible to detect that a curve of the corresponding wavelength moves to the left in the wavelength spectrum curve of the reflected light as shown in FIG. 4. On the contrary, if the sensing unit is deflected downward opposite to the direction A, the wavelength spectrum curve may move reversely.

Meanwhile, when the sensing unit is bent to the left in FIG. 10, the grating interval of the grating node located in the bent region of the second FBG sensor 400 is decreased, so that it may be detected that the curve of the corresponding wavelength is shifted to the left in the wavelength spectrum of the reflected light. If the sensing unit is bent to the right on the contrary, the wavelength spectrum curve will be shifted opposite to the above.

By using this principle, it is possible to know the bending direction by analyzing the change of wavelength of the reflected light output from two FBG sensors.

Furthermore, it will be understood that the bending direction can also be calculated using more than three FBG sensors.

Therefore, if the angle/direction detection sensor 200 is configured to include a plurality of FBGs, it is possible to know the curvature and the bending direction of the sensing unit 260.

Figure 11:
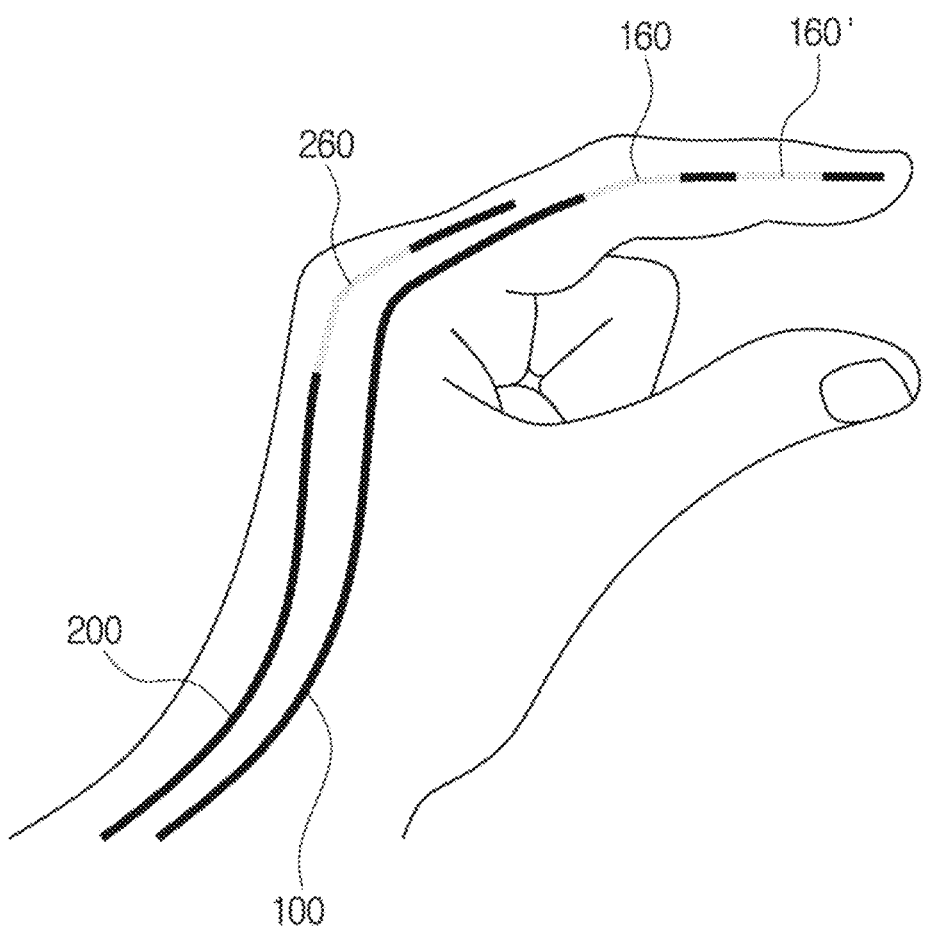
FIG. 11 shows an angle detection sensor and an angle/direction detection sensor disposed at a finger joint.

FIG. 11 shows that the angle detection sensor 100 and the angle/direction detection sensor 200 are disposed at a finger joint.

A first joint linking the palm and the finger is a multi-DOF joint which is capable of moving in various directions, and the angle/direction detection sensor 200 is disposed corresponding to the position of the first joint. The sensing unit 260 of the angle/direction detection sensor 200 aligns with the first joint to provide information on the bending angle and the bending direction of the first joint.

The second and third joints of the finger formed after the first joint correspond to a 1-DOF joint which is capable of bending only in one direction. The angle detection sensor 100 may be disposed at the second joint and the third joint.

The separate angle detection sensor 100 may be disposed separately at each the second joint and the third joint, respectively, but in this embodiment, the angle detection sensor 100 of a single strand is disposed over the second joint and the third joint.

Referring to FIG. 11, the angle detection sensor 100 has two sensing units 160, 160' corresponding to the positions of the second joint and the third joint. That is, a plurality of sensing units are arranged in a single angle detection sensor 100.

The intervals between gratings constituting two sensing units 160, 160' are formed different from each other so that the wavelength spectrums of the reflected light do not overlap with each other. If two sensing units 160, 160' have four grating nodes, respectively, all grating intervals forming eight grating nodes in total should be formed differently.

According to this configuration, the bending angles of two joints, namely the second joint and the third joint, over which a single angle detection sensor 100 is provided, may be calculated.

If a single-stranded sensor of the same kind may be arranged to pass through several joints, it is possible to reduce the number of motion sensors by forming sensing units as many as the number of joints.

Even though it has been described in this embodiment that a single sensing unit has a plurality of grating nodes, a single sensing unit may also have a single grating node. In this case, in FIG. 4, only the reflected light spectrum corresponding to one peak will appear.

FIGS. 12 to 16B show that a plurality of motion sensors 2 are applied to a body of a user.

According to this embodiment, for example, the angle detection sensor 100 is applied to a 1-DOF joint which is bendable only in one direction, like an elbow joint, since the bending direction is fixed.

Meanwhile, in case of a multi-DOF joint which is bendable in various directions, like as a wrist joint, its bending angle and direction should be known in order to simulate its motion. For this, the angle/direction detection sensor 200 is applied.

In addition, in case of a human body portion which is rotatable, like an upper arm, an upper arm, a thigh and a calf, the rotation direction of the joint should be known, and thus angle/direction detection sensor 200 is applied in order to simulate the motion. The change in position of the tip of the sensor at the portion where the rotation occurs is measured to measure the degree of rotation in the joint in the axis direction.

However, since the angle/direction detection sensor 200 includes an angle measurement function, the angle/direction detection sensor 200 may also be applied to a 1-DOF joint.

As described above, since the angle detection sensor 100 includes a single FBG sensor and the angle/direction detection sensor 200 includes three FBG sensors, there are many FBG sensors for which the angle/direction detection sensor 200 needs to analyze the spectrum. In addition, the angle/direction detection sensor 200 is generally larger than the angle detection sensor 100 and is not easily manufactured.

Therefore, by applying the angle detection sensor 100 to a 1-DOF joint, it is possible to reduce the amount of calculation and the manufacturing cost and simplify the device.

In FIGS. 12 to 16B, subscripts added to 100 or 200 for the motion sensor of each part refer to portions of a human body to which the motion sensor is applied.

Figure 13:
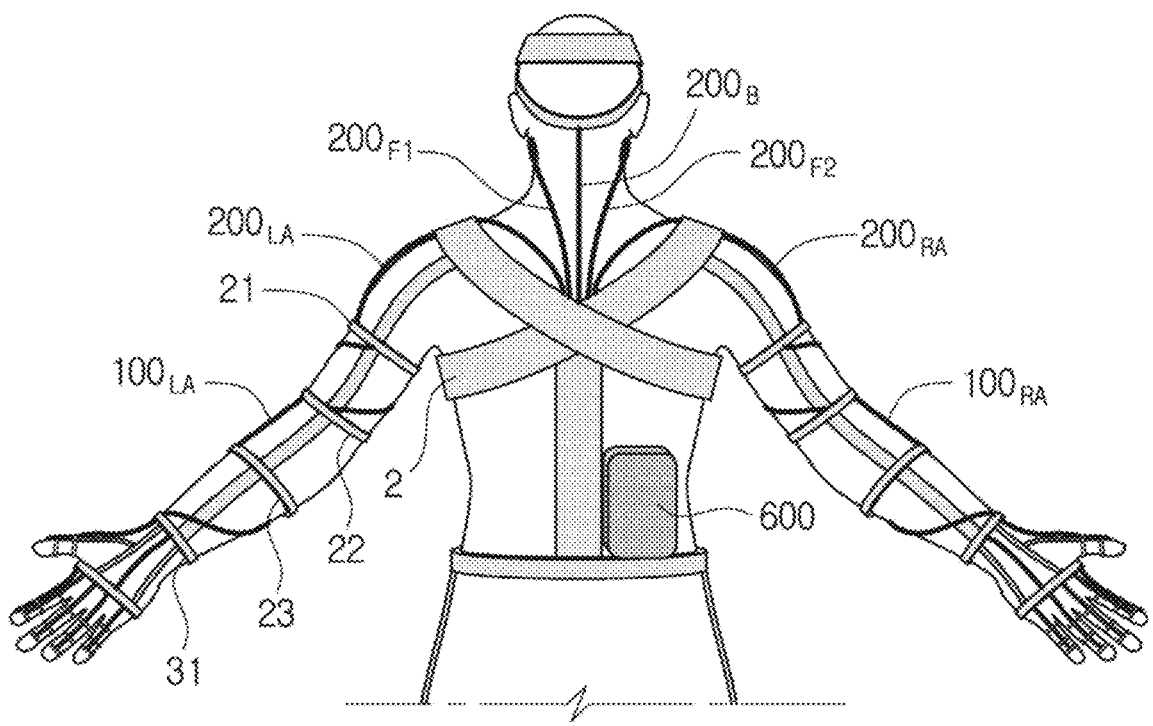
Figure 14:
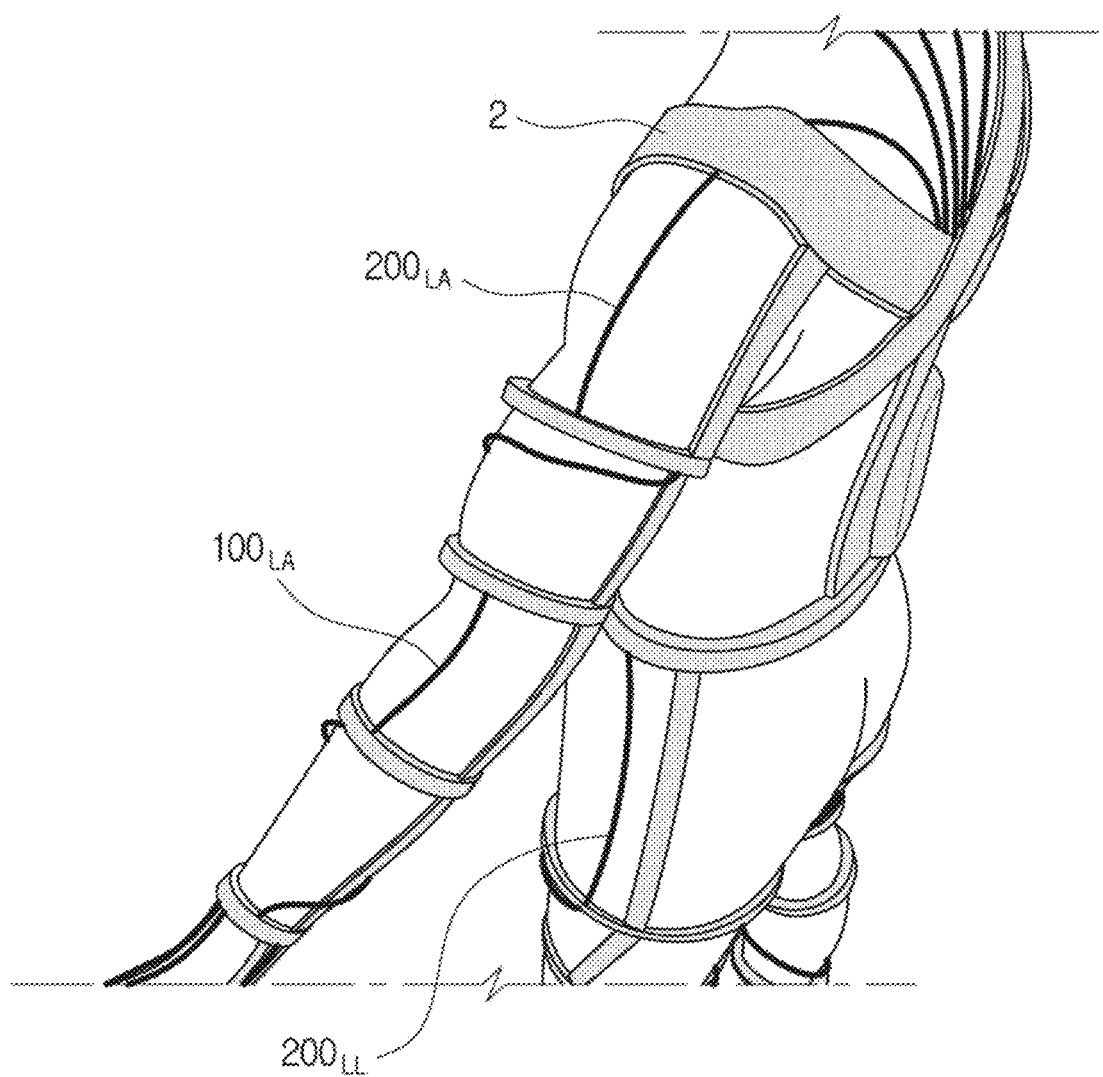
Figure 15:
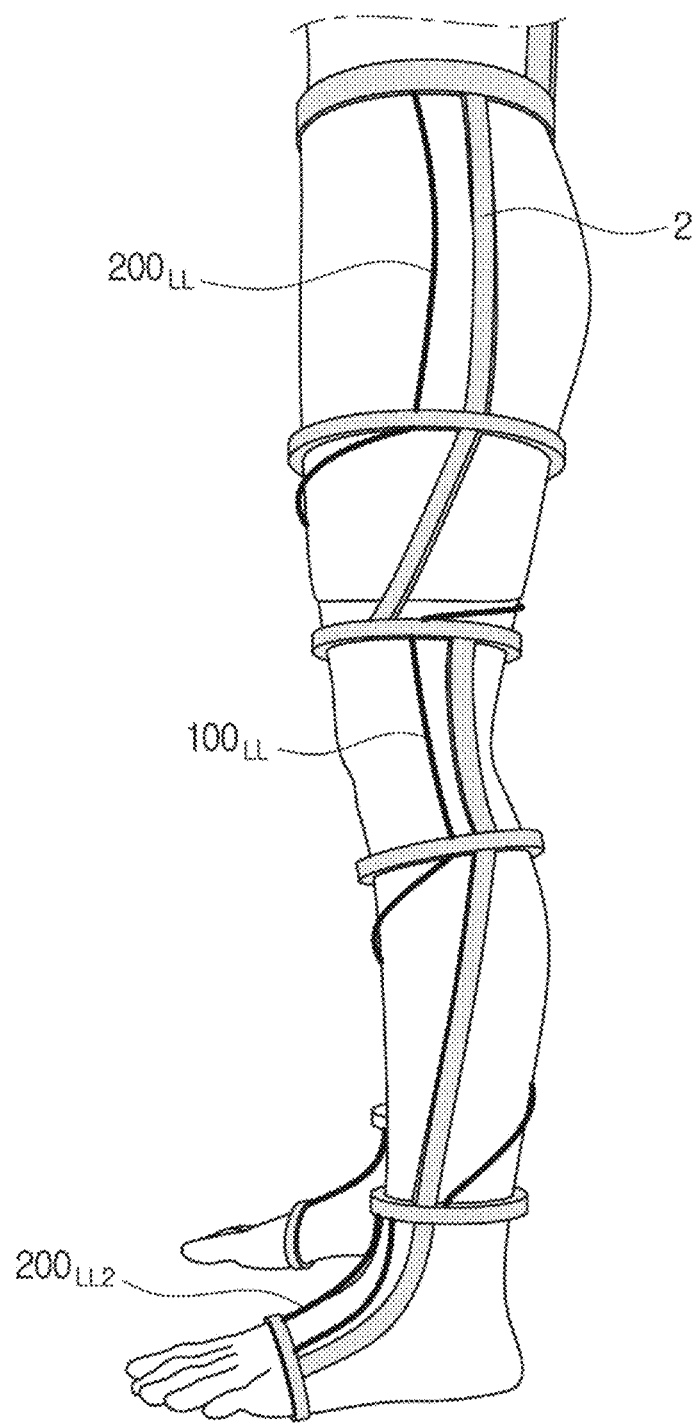

As shown in FIG. 13 in a best way, the motion capture system includes a control box 600 sized for the user to carry on the waist.

Figure 18:
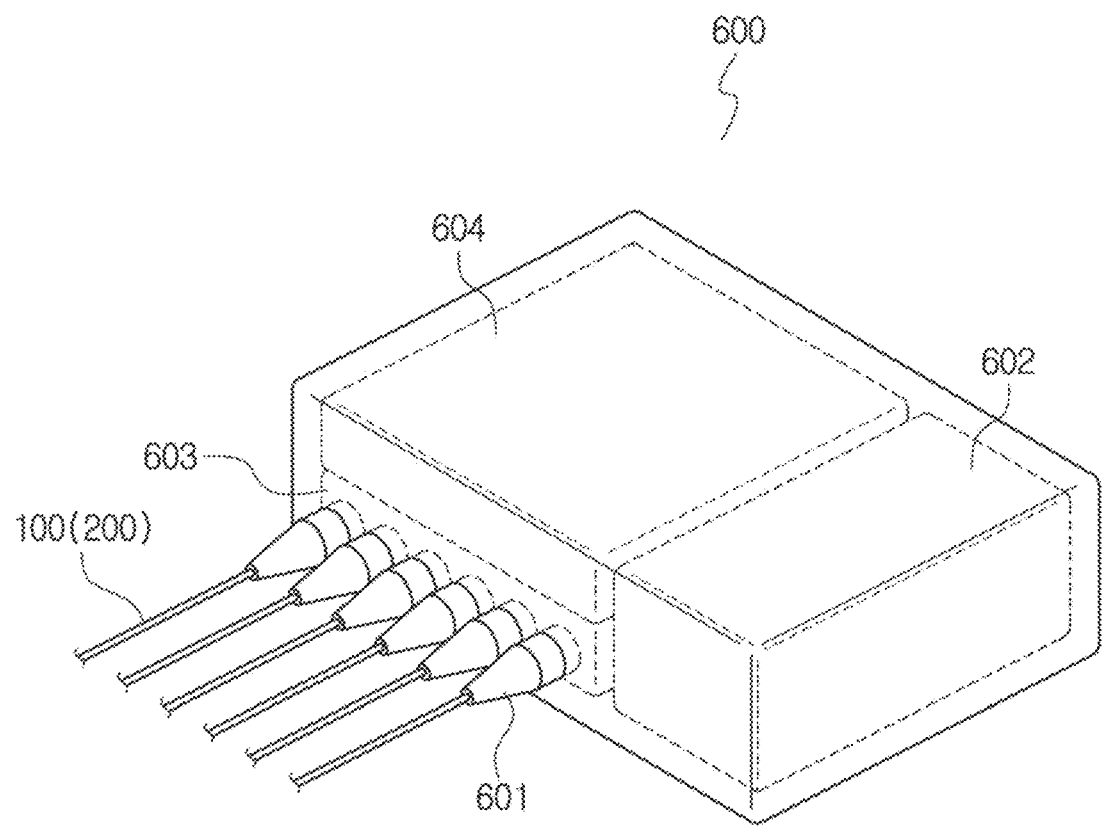
FIG. 18 is a diagram conceptually showing a control box.

FIG. 18 is a diagram conceptually showing a control box 600.

As shown in FIG. 18, the control box 600 includes a light source 603 for irradiating light to the motion sensor 2, and the angle detection sensor 100 and/or the angle/direction detection sensor 200 extending to each part of a human body through a connector 601 is connected to the light source 603.

Even though FIG. 18 depicts five connectors 601 and five sensors for convenience of illustration, the connectors 601 may be provided corresponding to the number of the angle detection sensor 100 and the angle/direction detection sensor 200 used. The light source 603 may include a distributor for distributing the reflected light output from the motion sensor.

The spectrum of the reflected light output from the angle detection sensor 100 and the angle/direction detection sensor 200 is analyzed through a measurer 604. The measurer 604 analyzes the spectrum of the reflected light respectively output from the angle detection sensor 100 and the angle/direction detection sensor 200 (the angle detection sensor 100 includes one (or two) reflected light, and the angle/direction detection sensor 200 includes three reflected lights), and calculates the bending angle (and the bending direction) of the joint corresponding to the sensing unit of each sensor.

The control box 600 may include a rechargeable battery 602 to be portable, and may also include a wired/wireless communication device capable of transmitting motion information of the joint, calculated through the measurer 604, to a controller for controlling the averter V.

Referring to FIGS. 12 to 16B again, a plurality of motion sensors extend from the control box 600 to each part of the human body.

Even though FIG. 13 depicts that only five-strand motion sensors are facing the control box 600, it should be understood that other motion sensors extend underneath a band and strip of the fixture 2 extending upwardly at a side of the control box 600.

A single-strand motion sensor $200_{RA}$ extending from the control box 600 to the right arm passes over the shoulder joint and surrounds the upper arm, and then surrounds the lower arm (the forearm) via the elbow and extends to the wrist.

Figure 17:
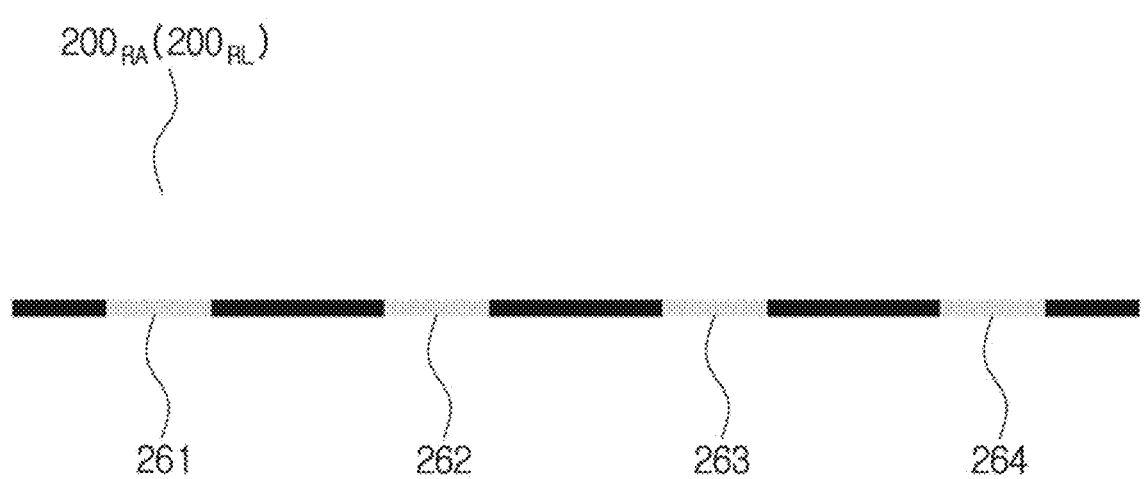
FIG. 17 is a schematic view showing a motion sensor applied to an arm (or, a leg).

FIG. 17 is a schematic view showing a motion sensor $200_{RA}$. The motion sensor $200_{RA}$ of this embodiment is an angle/direction detection sensor and includes four sensing units 261, 262, 263, 264 spaced apart from each other.

The first sensing unit 261 is disposed to correspond to the position of the shoulder joint, and the second sensing unit 262 is disposed to be positioned at a sensor portion surrounding the upper arm. The third sensing unit 263 is arranged to be positioned at a sensor portion surrounding the lower arm, and the fourth sensing unit 264 is positioned to correspond to the position of the wrist joint.

Figure 16A:
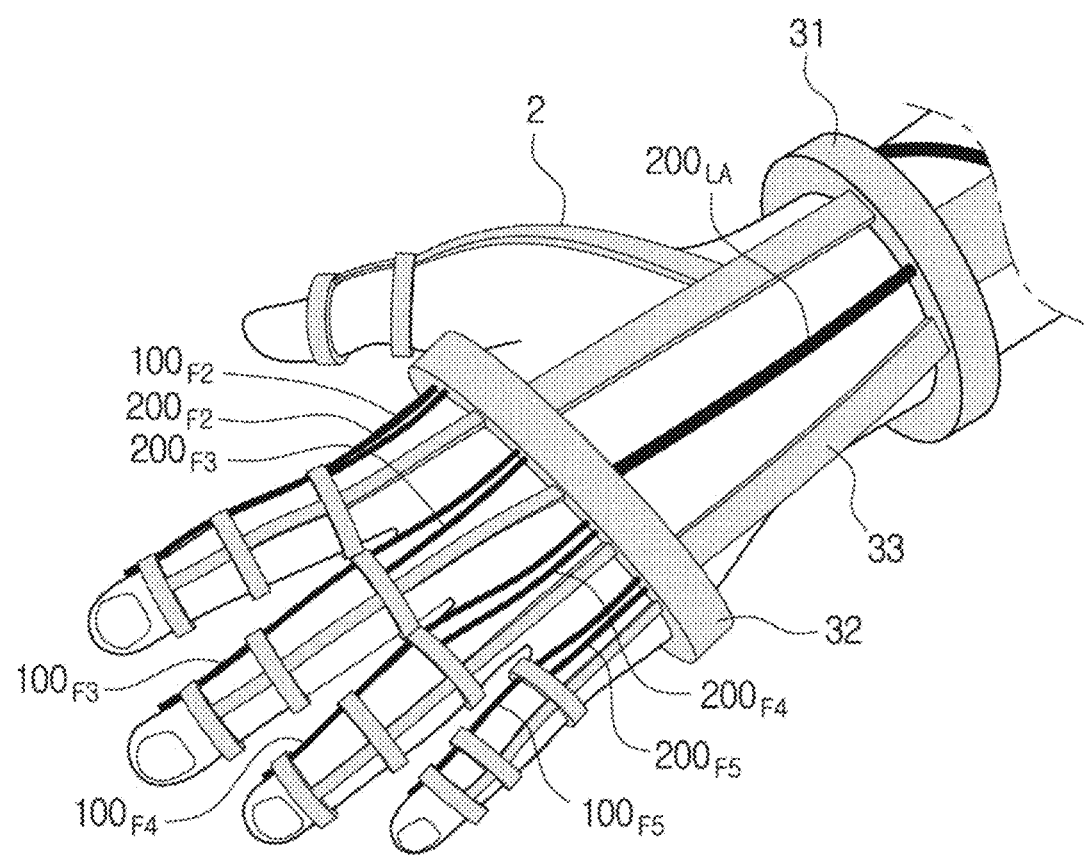

As shown in FIG. 16A in a best way, the fixture 2 includes bands 31, 32 surrounding knuckles (palm and forearm) connected through a joint such as a wrist joint, and a strip 33 connecting adjacent bands.

Two bands 31, 32 formed on two knuckles connected based on the wrist joint closely adhere and tightly fix the motion sensor $200_{LA}$ to the wrist. The fourth sensing unit 264 of the motion sensor $200_{LA}$ is fixed so as to extend over the wrist joint in order to measure the motion of the wrist joint.

Accordingly, the fourth sensing unit 264 of the motion sensor $200_{LA}$ may accurately bend in response to the motion of the wrist joint.

If the fourth sensing unit 264 of the motion sensor $200_{LA}$ located at the wrist joint is not aligned with the position of the wrist joint, the motion sensor $200_{LA}$ may be pulled or pushed slightly between two bands 31, 32 so that the sensing unit 264 aligns the position of the wrist joint.

The aligned motion sensor $200_{LA}$ may be connected to the two bands 31 and 32 by clips (not shown) or the like so as to be fixed without changing their positions.

Meanwhile, the motion sensor $200_{RA}$ may be formed longer than the length of the arm. After the sensor units 261, 262, 263, 264 are fixed at predetermined positions, the residual sensors remaining between two adjacent sensing units may be inserted into the fixture or wound around the fixture for storage.

The reflected light output from the first sensing unit 261 located at the shoulder joint is analyzed to measure the motion of the shoulder according to the bending angle and the bending direction of the shoulder joint.

The reflected light output through the second sensing unit 262 located at the upper arm is analyzed to measure a rotation state of the upper arm with respect to the shoulder. The reflected light output through the third sensing unit 263 located at the lower arm is analyzed to measure a rotation state of the lower arm with respect to the elbow.

Referring to FIG. 13, when the upper arm rotates, the band 22 bound to a lower side of the upper arm relatively rotates more than the band 21 bound to an upper side of the upper arm due to the structural characteristic of the human body, thereby causing the change of shape of the second sensing unit 262 located at the upper arm. As described above, the rotation state of the upper arm may be measured by changing the shape of the second sensing unit 262. In the same way, when the lower arm rotates, the band 31 bound to a lower side of the lower arm adjacent to the wrist rotates relatively more under the band 23 bound to an upper side of the lower arm, thereby causing the change of shape of the third sensing unit 263. The rotation state of the lower arm may be measured by changing the shape of the third sensing unit 263.

The reflected light output through the fourth sensing unit 264 located at the wrist joint is analyzed to measure the motion of the wrist according to the bending angle and the bending direction of the wrist joint.

According to this embodiment, the single-strand motion sensor $200_{RA}$ which is an angle/direction detection sensor having four sensing units 261, 262, 263, 264 may be used to capture all of the motions from the shoulder to the wrist (except for the elbow).

Meanwhile, since the elbow corresponds to a 1-DOF joint, in this embodiment, the motion of the elbow joint is measured and captured using the motion sensor $100_{RA}$ which is an angle detection sensor.

According to this embodiment, the motion sensor $100_{RA}$ has a single sensing unit, and the sensing unit is arranged to align with the elbow joint to measure the motion of the elbow.

In the left arm, the motion sensor $200_{LA}$ which is an angle/direction detection sensor and the motion sensor $100_{LA}$ which is an angle detection sensor are extended to measure the motion of the left arm, identical to the right arm. The structure, function and arrangement of the motion sensor $200_{LA}$ and the motion sensor $100_{LA}$ are the same as the motion sensor $200_{RA}$ and the motion sensor $100_{RA}$, respectively.

Figure 16B:
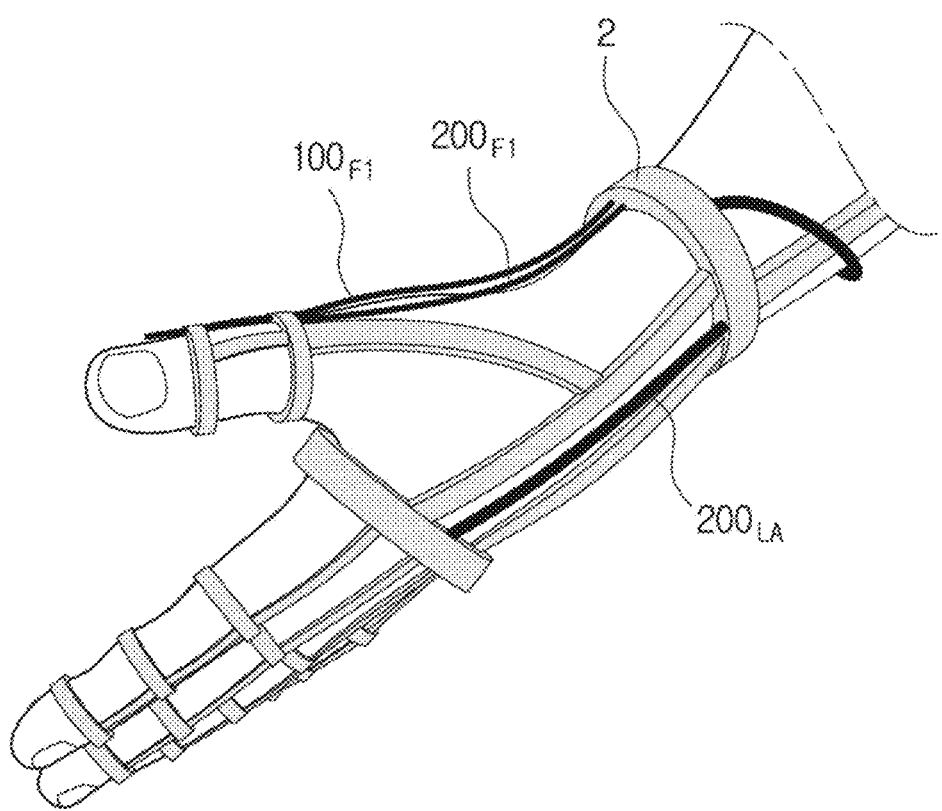

Meanwhile, referring to FIGS. 16A and 16B, a single motion sensor which is an angle/direction detection sensor and a single motion sensor which is an angle detection sensor extend at each finger.

On the thumb, a motion sensor $200_{F1}$ which is an angle/direction detection sensor is disposed above the first joint connected to the palm of the hand. The sensing unit of the motion sensor $200_{F1}$ is arranged to align with the position of the first joint to measure the bending angle and direction of the first joint.

A motion sensor $100_{F1}$ which is an angle detection sensor is disposed to pass the 1-DOF second joint located next to the first joint. The sensing unit of the motion sensor $100_{F1}$ is arranged to align with the position of the second joint to measure the bending angle of the second joint.

Though FIGS. 16A and 16B depict that the motion sensor $200_{F1}$ and the motion sensor $100_{F1}$ extend only above the hand, the remaining motion sensors not having a sensing unit extend to the control box 600 through the interior of the fixture 2.

On the index finger, a motion sensor $200_{F2}$ which is an angle/direction detection sensor is disposed above the first joint connected to the palm of the hand. The sensing unit of the motion sensor $200_{F2}$ is arranged to align with the position of the first joint to measure the bending angle and direction of the first joint of the index finger.

A motion sensor $100_{F2}$ which is an angle detection sensor is disposed to extend to the 1-DOF second joint and the 1-DOF third joint positioned next to the first joint. The motion sensor $100_{F2}$ has two sensing units, and the two sensing units are arranged to align with the positions of the second joint and the third joint, respectively, to measure the bending angle of the second joint and the third joint.

Motion sensors $200_{F3}$, $200_{F4}$, $200_{F5}$ which are angle/direction detection sensors are also disposed on the middle finger, the ring finger and the little finger connected to the palm of the hand, and motion sensors $100_{F3}$, $100_{F4}$, $100_{F5}$ which are angle detection sensors are disposed to extend to the second joint and the third joint.

The principle of measuring and capturing a motion of each finger has been described above with reference to FIG. 11.

Although it has been described with reference to the left hand, it will be understood that motion sensors are disposed at the right hand in the same manner as the left hand.

According to this embodiment, it is possible to measure motions of hand joints, which is a body organ moving most elaborately, by using 12-strand motion sensors, namely two-strand motion sensors extending along the arm and two-strand motion sensors disposed at each finger.

Meanwhile, a one-strand motion sensor $200_{RL}$ extending from the control box 600 to one leg passes through a hip joint and surrounds around the thigh, and then surrounds the calf via the knee and extends to the ankle.

As shown in FIG. 17, the motion sensor $200_{RL}$ may have the same structure as the motion sensor $200_{RA}$.

That is, the motion sensor $200_{RL}$ of this embodiment is an angle/direction detection sensor and includes four sensing units 261, 262, 263, 264 spaced apart from each other.

The first sensing unit 261 of the motion sensor $200_{RL}$ is arranged to correspond to the position of the hip joint, and the second sensing unit 262 is arranged to be positioned at the sensor region surrounding the thigh. The third sensing unit 263 is arranged to be positioned at the sensor region surrounding the calf, and the fourth sensing unit 264 is positioned to correspond to the position of the ankle joint.

The reflected light output from the first sensing unit 261 located at the hip joint is analyzed to measure the motion of the hip joint according to the bending angle and the bending direction of the hip joint. The reflected light output through the second sensing unit 262 located at the thigh is analyzed to measure the rotation state of the thigh. The reflected light output through the third sensing unit 263 located at the calf is analyzed to measure the rotation state of the calf. The reflected light output through the fourth sensing unit 264 located at the ankle joint is analyzed to measure the motion of the ankle according to the bending angle and the bending direction of the ankle joint.

According to this embodiment, a motion sensor $200_{RL2}$ which is an angle/direction detection sensor is formed over the ankle joint approximately parallel to the motion sensor $200_{RL}$ at the ankle portion, thereby adding reliability to the measurement of motion of the multi-DOF ankle. This additional motion sensor can be further applied to the wrist.

It is possible to capture all of the motions from the hip joint to the ankle (except for the knee) by using the one-strand motion sensor $200_{RL}$ which is an angle/direction detection sensor having four sensing units 261, 262, 263, 264.

Meanwhile, since the knee corresponds to a 1-DOF joint, in this embodiment, the motion of the knee joint may be measured and captured using the motion sensor $100_{RL}$ which is an angle detection sensor.

According to this embodiment, the motion sensor $100_{RL}$ has a single sensing unit, and the sensing unit is arranged to align with the knee joint to measure the motion of the knee.

At the left leg, a motion sensor $200_{LL}$ which is an angle/direction detection sensor and a motion sensor $100_{LL}$ which is an angle detection sensor are extended in the same manner as the right leg to measure the motion of the left leg. The structure, function and arrangement of the motion sensor $200_{LL}$ and the motion sensor $100_{LL}$ are the same as the motion sensor $200_{RL}$ and the motion sensor $100_{RL}$, respectively.

Figure 12:
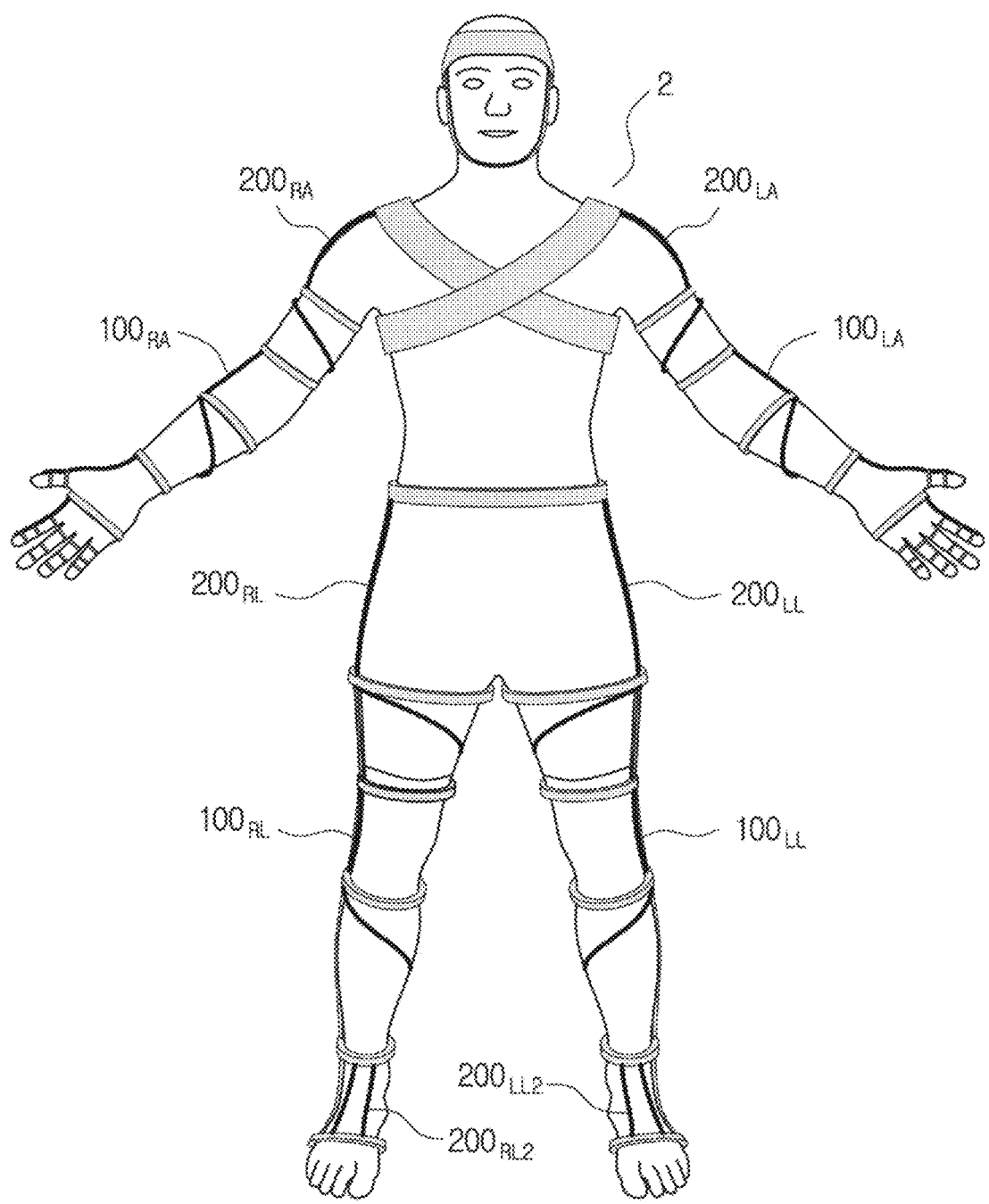
FIGS. 12 to 16B show that a plurality of motion sensors are applied to a body of a user.

As shown in FIGS. 12 and 13, a motion sensor $200_B$ using an angle/direction detection sensor is disposed to detect the motion of joints of the waist and the neck. The motion sensor $200_B$ is connected to the rear head along the waist line. The motion sensor $200_B$ may include a sensing unit that substantially spans the entire waist length to detect the bending angle, the bending direction and the rotation amount of the entire waist.

Two motion sensors $200_{F1}$, $200_{F2}$ using an angle/direction detection sensor extend to a side of the neck and extend to a side of the face to detect the motion of the face with respect to the neck. By using two motion sensors $200_{F1}$, $200_{F2}$, the motion of the face having a relatively high DOF may be measured.

According to this embodiment, it has been described that the fixture 2 is made in a body-worn type, and all the motion sensors are connected to the single control box 600, but the present disclosure is not limited thereto.

Figure 19A:
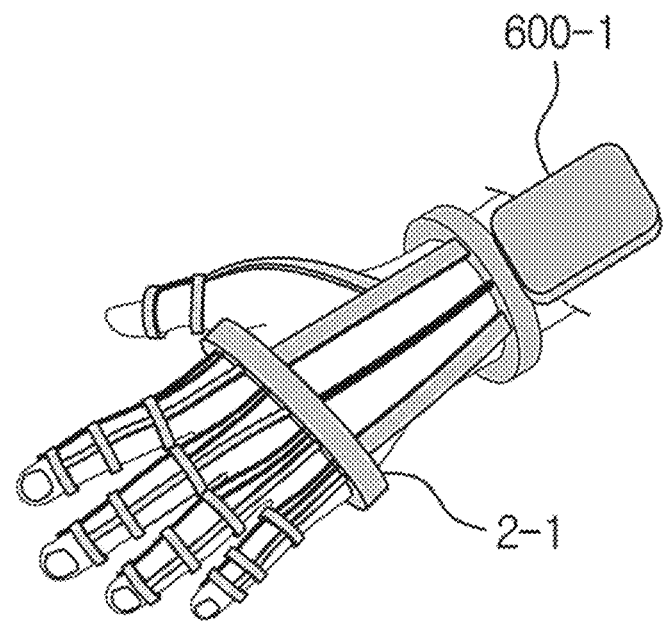
FIG. 19A to 19C shows a motion capture system modulated for each portion of a human body.
Figure 19B:
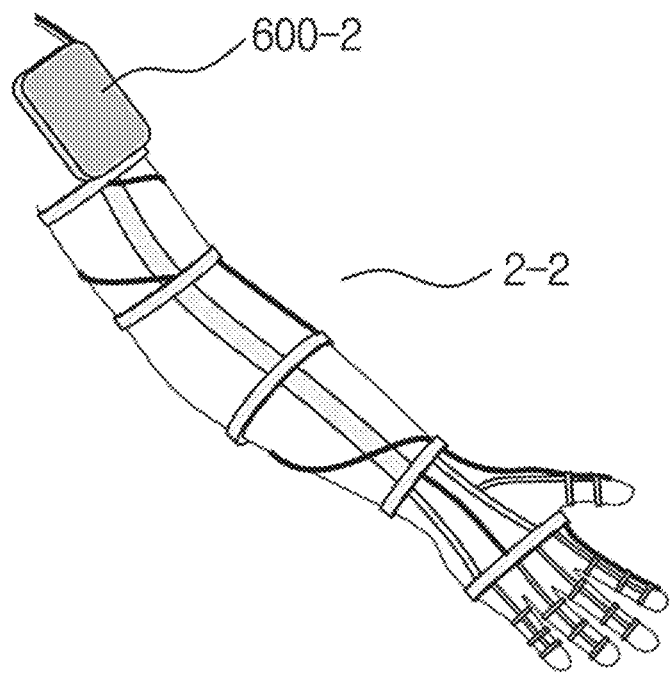
Figure 19C:
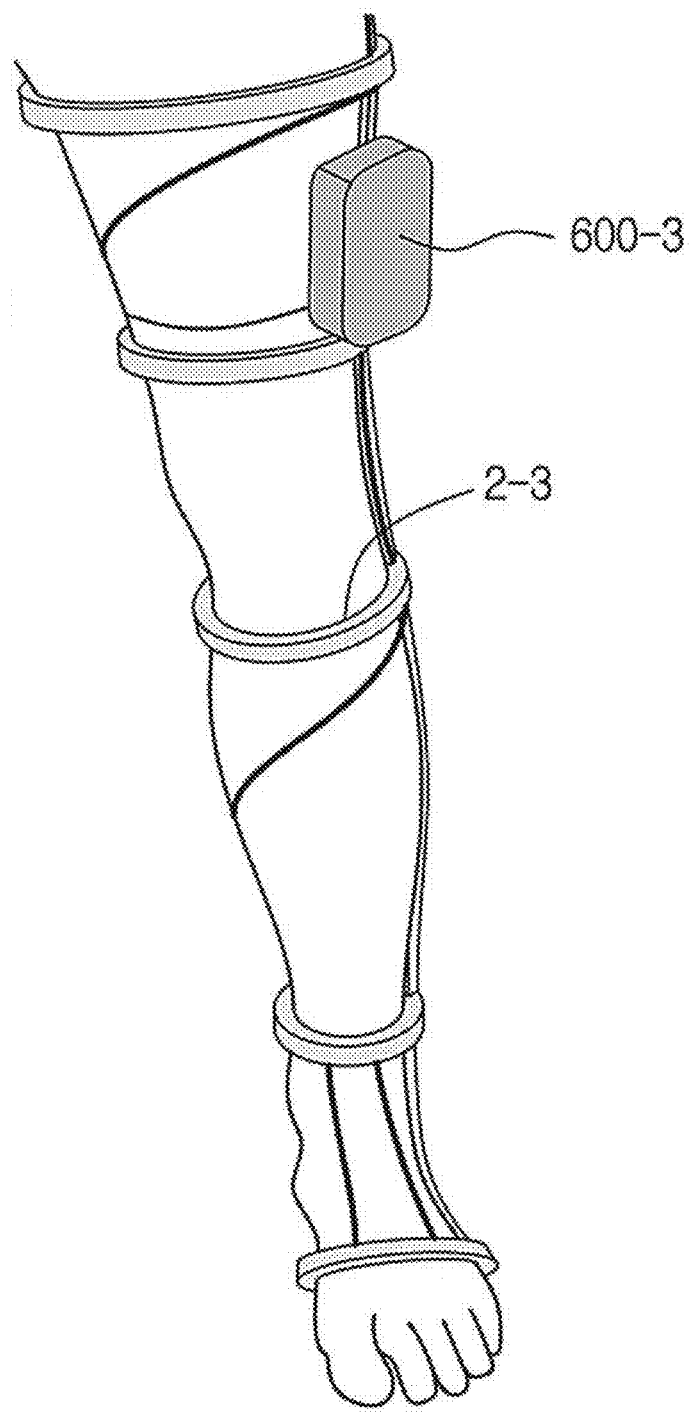

FIG. 19A to 19C shows a modulated motion capture system.

As shown in FIG. 19A to 19C, if necessary, fixtures 2-1, 2-2, 2-3 may be formed separately for each part, namely the hand (FIG. 19A), the arm (FIG. 19B) and the leg (FIG. 19C). Also, control boxes 600-1, 600-2, 600-3 may be attached to the part, respectively, and motion sensors provided in each part may be modularized to be connected to the control box(s) (e.g., 600-1, 600-2, 600-3).

The user may wear each modularized motion capture device on a required body portion. If all the modules are worn, the modules may perform the same operation as the whole-body type device described above.

In addition, in this embodiment, it is described that the fixture 2 is formed in a band shape, the present disclosure is not limited thereto.

Figure 20:
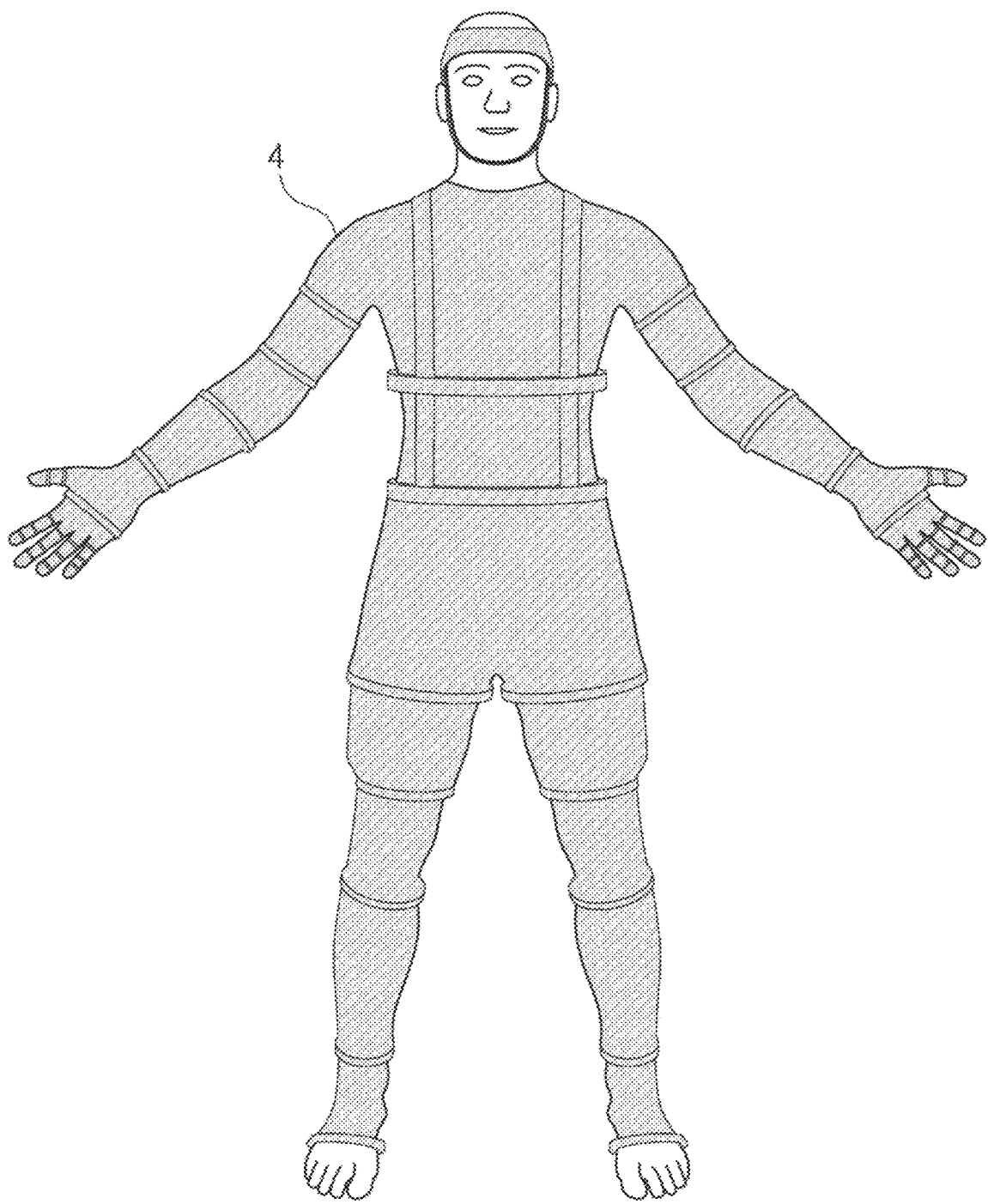
FIG. 20 shows a fixture according to another embodiment.

FIG. 20 shows a fixture 4 according to another embodiment.

The fixture 4 of this embodiment includes a plurality of motion sensors embedded therein and has an elastic cloth form which may be closely adhered to the skin. Here, the cloth may include not only suits but also any types of cloth such as gloves, shoes and caps, which the user may wear.

If this fixture 4 is used, when a user wears custom-made cloth, motion sensors may be substantially arranged at each joint, and thus motion capture is allowed through a simple data correction operation.

However, the shape of the fixture 4 is not limited to the band type or the cover type as described above, and the motion sensor may also be fixed to the skin of the user by means of adhesion or by using a pressure band or the like.

If the sensing unit of the motion sensor is aligned to each joint and the motion sensor may be fixed to a human body to be bent well corresponding to the motion of the joint, they may be used as the fixture according to the present disclosure.

According to the motion capture system of this embodiment, it is possible to simultaneously measure joint motions of 35 DOF or more in total throughout the human body. In particular, complex and elaborate movements of the hand and the fingers up to 22 DOF may be measured simultaneously for each joint.

In addition, by using the FBG sensor, it is possible to measure minute changes of several nm, and it is possible to manufacture motion sensors with various lengths and shapes, which may diversify the resolution and range of measurement. Also, a so-called drift phenomenon caused by long-term use does not occur.

Therefore, motion capture with very high accuracy and reliability is possible.

The information on the bending angle and the bending direction of each joint of a human body calculated by the motion capture system may be converted into information for moving each joint of the averter V to control the averter V precisely. This enables, very sophisticated control of the motion in which the angle and position of the hand of an averter should be accurately calculated, for example, like a case where two averters controlled by different users in one virtual space shake hands with each other.

Moreover, the motion capture system of this embodiment may capture the motion without space limitation when the control box is configured with a portable compact structure. Since the motion sensor is made of a very light material, it is possible to minimize the restriction of the movement of the user by wearing the motion sensor on the human body by means of a suitable fixture.

What is claimed is:
1. A motion capture system, comprising:
    a motion sensor having a flexible body and a plurality of fiber bragg gratings (FBG) sensors inserted into the flexible body;
    a fixture configured to fix the motion sensor to a human body of a user;
    a light source configured to irradiate light to the motion sensor; and
    a measurer configured to analyze a reflected light output from the motion sensor, wherein each of the FBG sensors includes an optical fiber and a sensing unit formed in a partial region of the optical fiber and having a plurality of gratings, wherein the motion sensor includes one or more of an angle detection sensor and an angle/direction detection sensor, the angle detection sensor being configured to measure an angle for a 1-DOF (degree of freedom) joint which is bendable only in one direction, the angle/direction detection sensor being configured to measure motions of a multi-DOF joint which is bendable in a plurality of directions, wherein the angle/direction detection sensor is further configured to measure a presence of rotation and a rotation amount by calculating a position change of a tip of the sensing unit, and wherein a change of a wavelength spectrum of the reflected light, caused by a change of an interval of the gratings due to a motion of the user, is detected to measure a motion state of the user.

2. The motion capture system according to claim 1,
wherein the sensing unit of the motion sensor is further configured to be disposed on a joint of the user, and
wherein the angle detection sensor includes the sensing unit to calculate a bending angle of the joint by means of the change of the wavelength spectrum.

3. The motion capture system according to claim 1,
wherein the angle/direction detection sensor includes the sensing unit to calculate a bending angle, a bending direction and a rotating direction of a joint of the human body by means of the change of the wavelength spectrum.

4. The motion capture system according to claim 2,
wherein the sensing unit of the angle detection sensor is configured to be disposed at the 1-DOF (degree of freedom) joint.

5. The motion capture system according to claim 2,
wherein the sensing unit includes a plurality of grating nodes each having a plurality of gratings,
wherein the plurality of gratings are arranged at a same interval in each of the plurality of grating nodes, and
wherein intervals between gratings of the grating nodes are different for each grating node.

6. The motion capture system according to claim 5,
wherein the angle detection sensor includes a plurality of FBG sensors,
wherein a longitudinal central axis of the plurality of FBG sensors is spaced apart from a longitudinal central axis of the flexible body, and
wherein the grating nodes of the FBG sensors along a longitudinal direction of the angle detection sensor are located not to overlap each other.

7. The motion capture system according to claim 6,
wherein the body has a quadrilateral cross section, when being observed in a longitudinal direction.

8. The motion capture system according to claim 3,
wherein the sensing unit of the angle/direction detection sensor is configured to be disposed at the 1-DOF joint which is bendable in only one direction, at the multi-DOF joint, or at a part of the human body which is rotatable based on a single joint.

9. The motion capture system according to claim 3,
wherein the angle/direction detection sensor includes a plurality of FBG sensors, and
wherein a longitudinal central axis of the plurality of FBG sensor is spaced apart from a longitudinal central axis of the flexible body.

10. The motion capture system according to claim 9,
wherein the angle/direction detection sensor includes three FBG sensors provided at an interval of 120 degrees based on the longitudinal central axis of the flexible body.

11. The motion capture system according to claim 3,
wherein the sensing unit includes a plurality of grating nodes each having a plurality of gratings,
wherein the plurality of gratings are arranged at a same interval in each of the plurality of grating nodes, and
wherein intervals between gratings of the grating nodes are different for each grating node.

12. The motion capture system according to claim 3,
wherein the angle/direction detection sensor is configured to extend to surround the human body between joints, and
wherein the sensing unit of the angle/direction detection sensor is configured to be disposed at the human body between the joints.

13. The motion capture system according to claim 1,
wherein the motion sensor includes a plurality of sensing units, respective sensing units having different intervals between gratings, and
wherein the plurality of sensing units are configured to be disposed corresponding to different portions of the human body.

14. The motion capture system according to claim 1,
wherein the fixture includes a band configured to surround knuckles connected through the joint, and
wherein the flexible body of the motion sensor is fixed to two bands formed at two knuckles connected through the joint.

15. The motion capture system according to claim 1,
wherein the motion sensor is attached to the fixture, and the fixture is cloth which is wearable by the user.

16. The motion capture system according to claim 1,
wherein the motion capture system is configured to be worn on the human body by modularization on required body portions.

17. The motion capture system according to claim 16,
each of motion sensors of modules for the modularization is connected to control boxes, respectively.

18. The motion capture system according to claim 1, further comprising:
a control box sized to carry on a waist of the user, including a light source, connector and a measurer, the connector connecting the motion sensor with the light source.

* * * * *